United States Patent
Le Neel et al.

(10) Patent No.: US 9,027,400 B2
(45) Date of Patent: May 12, 2015

(54) TUNABLE HUMIDITY SENSOR WITH INTEGRATED HEATER

(75) Inventors: Olivier Le Neel, Singapore (SG); Suman Cherian, Kerala (IN); Ravi Shankar, Singapore (SG); Boon Nam Poh, Singapore (SG); Sebastien Marsanne, Singapore (SG); Michele Vaiana, San Giovanni La Punta (IT)

(73) Assignees: STMicroelectronics Pte Ltd., Singapore (SG); STMicroelectronics Asia Pacific Pte Ltd., Singapore (SG); STMicroelectronics S.R.L., Agrate Brianza (IT)

( * ) Notice: Subject to any disclaimer, the term of this patent is extended or adjusted under 35 U.S.C. 154(b) by 500 days.

(21) Appl. No.: 13/310,477

(22) Filed: Dec. 2, 2011

(65) Prior Publication Data

US 2013/0139587 A1   Jun. 6, 2013

(51) Int. Cl.
*G01N 27/22* (2006.01)

(52) U.S. Cl.
CPC .................................... *G01N 27/223* (2013.01)

(58) Field of Classification Search
CPC ... G01N 27/223; G01N 27/225; G01N 27/22; G01N 27/02; G01N 27/221
USPC ...................................................... 73/335.04
See application file for complete search history.

(56) References Cited

U.S. PATENT DOCUMENTS

| | | | |
|---|---|---|---|
| 2,648,823 A | 8/1953 | Kock et al. | |
| 2,717,356 A | 9/1955 | Foster | |
| 2,735,934 A | 2/1956 | Keizer et al. | |
| 3,083,573 A * | 4/1963 | Shaw | 73/335.04 |
| 3,210,607 A | 10/1965 | Flanagan | |
| 3,323,084 A | 5/1967 | Glanc | |
| 3,500,243 A | 3/1970 | Polin | |
| 3,854,337 A | 12/1974 | Moran et al. | |
| 3,971,661 A * | 7/1976 | Lindberg et al. | 430/312 |
| 4,017,820 A | 4/1977 | Ross | |
| 4,217,623 A * | 8/1980 | Nishino et al. | 361/280 |
| 4,433,319 A * | 2/1984 | Luder et al. | 338/34 |
| 4,482,882 A * | 11/1984 | Luder et al. | 338/34 |
| 4,500,940 A * | 2/1985 | Kuisma et al. | 361/286 |

(Continued)

FOREIGN PATENT DOCUMENTS

| | | |
|---|---|---|
| EP | 0 822 579 A1 | 2/1998 |
| EP | 1 324 382 A1 | 7/2003 |

(Continued)

OTHER PUBLICATIONS

Hautefeuille, Mathieu, et al. "Development of a microelectromechanical system (MEMS)-based multisensor platform for environmental monitoring." Micromachines 2.4 (Nov. 3, 2011): 410-430.*

(Continued)

*Primary Examiner* — Lisa Caputo
*Assistant Examiner* — Punam Roy
(74) *Attorney, Agent, or Firm* — Seed IP Law Group PLLC

(57) ABSTRACT

A capacitive humidity sensor includes a first electrode, a humidity sensitive dielectric layer, and a second electrode. The humidity sensitive dielectric layer is between the first and the second electrodes. The humidity sensitive dielectric layer is etched at selected regions to form hollow regions between the first and second electrodes.

18 Claims, 14 Drawing Sheets

(56) References Cited

U.S. PATENT DOCUMENTS

| | | | |
|---|---|---|---|
| 4,532,016 A * | 7/1985 | Chambaz et al. | 205/162 |
| 4,733,370 A | 3/1988 | Kitajima et al. | |
| 4,739,380 A | 4/1988 | Lauks et al. | |
| 4,761,710 A * | 8/1988 | Chen | 361/286 |
| 5,018,395 A | 5/1991 | Hickox et al. | |
| 5,204,541 A | 4/1993 | Smayling et al. | |
| 5,262,279 A * | 11/1993 | Tsang et al. | 430/311 |
| 5,522,980 A * | 6/1996 | Hobbs et al. | 204/432 |
| 5,640,013 A | 6/1997 | Ishikawa et al. | |
| 5,643,804 A | 7/1997 | Arai et al. | |
| 5,814,726 A * | 9/1998 | Mitter | 73/335.04 |
| 6,085,576 A | 7/2000 | Sunshine et al. | |
| 6,287,750 B1 * | 9/2001 | Sakurai | 430/313 |
| 6,412,919 B1 | 7/2002 | Ghozeil et al. | |
| 6,448,695 B2 | 9/2002 | Milsom | |
| 6,467,332 B1 | 10/2002 | Bertschi et al. | |
| 6,504,226 B1 | 1/2003 | Bryant | |
| 6,635,585 B1 * | 10/2003 | Khe et al. | 438/780 |
| 6,649,357 B2 | 11/2003 | Bryan et al. | |
| 6,806,553 B2 | 10/2004 | Yashima et al. | |
| 6,821,729 B2 | 11/2004 | Ackley et al. | |
| 6,883,364 B2 | 4/2005 | Sunshine et al. | |
| 6,933,807 B2 | 8/2005 | Marksteiner et al. | |
| 7,071,073 B2 | 7/2006 | Villa et al. | |
| 7,189,314 B1 | 3/2007 | Pace et al. | |
| 7,242,569 B2 | 7/2007 | Hunt et al. | |
| 7,294,536 B2 | 11/2007 | Villa et al. | |
| 7,364,896 B2 | 4/2008 | Schembri | |
| 7,368,312 B1 | 5/2008 | Kranz et al. | |
| 7,594,435 B2 * | 9/2009 | Sudo | 73/335.04 |
| 7,651,868 B2 | 1/2010 | McDevitt et al. | |
| 7,683,891 B2 * | 3/2010 | Tran | 345/173 |
| 7,733,319 B2 | 6/2010 | Aiba | |
| 8,079,256 B2 * | 12/2011 | Langenbacher et al. | 73/335.04 |
| 8,325,460 B2 * | 12/2012 | Park et al. | 361/286 |
| 8,363,379 B2 | 1/2013 | Edelstein et al. | |
| 8,650,953 B2 | 2/2014 | Cherian et al. | |
| 2003/0062807 A1 | 4/2003 | Takeuchi et al. | |
| 2003/0201450 A1 | 10/2003 | Yamazaki et al. | |
| 2004/0172798 A1 | 9/2004 | Ruby et al. | |
| 2005/0087787 A1 | 4/2005 | Ando | |
| 2005/0208696 A1 | 9/2005 | Villa et al. | |
| 2006/0125489 A1 | 6/2006 | Feucht et al. | |
| 2006/0171098 A1 | 8/2006 | Won | |
| 2006/0197118 A1 | 9/2006 | Migliorato et al. | |
| 2006/0257286 A1 | 11/2006 | Adams | |
| 2007/0290235 A1 | 12/2007 | Lehmann et al. | |
| 2010/0107739 A1 | 5/2010 | Marra | |
| 2010/0163410 A1 | 7/2010 | Mastromatteo et al. | |
| 2010/0170324 A1 | 7/2010 | Mastromatteo et al. | |
| 2011/0051309 A1 | 3/2011 | Furukawa et al. | |
| 2011/0146400 A1 * | 6/2011 | Humbert et al. | 73/335.04 |
| 2011/0179861 A1 * | 7/2011 | Grange et al. | 73/335.04 |
| 2011/0209524 A1 | 9/2011 | Ziglioli et al. | |
| 2011/0318840 A1 | 12/2011 | Ziglioli et al. | |
| 2012/0168882 A1 | 7/2012 | Cherian et al. | |
| 2012/0171713 A1 | 7/2012 | Cherian et al. | |
| 2013/0207673 A1 * | 8/2013 | Tondokoro et al. | 324/664 |

FOREIGN PATENT DOCUMENTS

| | | | | |
|---|---|---|---|---|
| EP | 1 403 383 A1 | 3/2004 | | |
| JP | 04364014 A | 12/1992 | | |
| WO | WO 2010006877 A1 * | 1/2010 | | H01G 5/013 |
| WO | 2011/085931 A1 | 7/2011 | | |

OTHER PUBLICATIONS

Benetti et al., "Chemical Sensor Based on Thin Film Bulk Acoustic Wave Resonator (TFBAR)," Proceedings of the 10th Italian Conference on Sensors and Microsystems, Firenze, Italy, pp. 326-331, Feb. 15-17, 2005.

Boser, "Capacitive Sensor Interfaces," Berkeley Sensor & Actuator Center, Department of Electrical Engineering and Computer Sciences, University of California, Berkeley, California, 40 pages, 1996.

D'amico et al., "Olfactometric Apparatus Based on Oscillating Crystal Sensors Functionalised With Tetrapyrrolic Macrocycles and Provided With Electronics for Conditioning and Reading the Signals, Communicating With a PC, Managing Through a Software and Analysis and Displaying the Data," Italian Patent Application No. RM2001A000455, filed Jul. 26, 2001, 20 pages w/ English translation.

Holmberg, "Automatic Balancing of Linear AC Bridge Circuits for Capacitive Sensor Elements," IEEE Transactions on Instrumentation and Measurement, 44(3):803-805, Jun. 1995.

Hwang et al., "CMOS VLSI Potentiostat for Portable Environmental Sensing Applications," IEEE Sensors Journal 10(4):820-821, Apr. 2010.

Kraver et al., "A mixed signal interface microinstrument," Sensors and Actuators A 91:266-277, 2001.

Matsumoto et al., "Influence of Underlayer Materials on Preferred Orientations of Sputter-Deposited AlN/Mo Bilayers for Film Bulk Acoustic Wave Resonators," Japanese Journal of Applied Physics 43(12):8219-8222, 2004.

Richter et al., "A High Performance Silicon Micropump for Fuel Handling in DMFC Systems," proceedings of the Fuel Cell Seminar, Miami Beach, FL, USA, pp. 272-275, Nov. 3-7, 2003.

Rosenbaum, "Bulk Acoustic Wave Theory and Devices," Boston, MA: Artech House, 1988, 7 pages.

Safari et al., "Ferroelectric Ceramics: Processing, Properties & Applications," URL=http://www.rci.rutgers.edu/~ecerg/projects/ferroelectric.html, 38 pages, last modified Aug. 28, 2000.

Schienle et al., "A Fully Electronic DNA Sensor With 128 Positions and In-Pixel A/D Conversion," IEEE Journal of Solid-State Circuits 39(12):2438-2445, Dec. 2004.

Sharma et al., "Integration of Precision Passive Components on Silicon for Performance Improvements and Miniaturization," $2^{nd}$ Electronics System-Integration Technology Conference, University of Greenwich, London, United Kingdom, Sep. 1-4, 2008, pp. 485-490.

St. Onge et al., "Design of Precision Capacitors for Analog Applications," IEEE Transactions on Components, Hybrids, and Manufacturing Technology, 15(6):1064-1071, Dec. 1992.

Turner et al., "A CMOS Potentiostat for Amperometric Chemical Sensors," IEEE Journal of Solid-State Circuits, SC-22(3):473-478, Jun. 1987.

Yang et al., "Amperometric Electrochemical Microsystem for a Miniaturized Protein Biosensor Array," IEEE Transactions on Biomedical Circuits and Systems 3(3):160-168, Jun. 2009.

Zhang et al., "Electrochemical Array Microsystem with Integrated Potentiostat," IEEE Sensors, pp. 385-388, 2005.

Dokmeci et al., "A High-Sensitivity Polyimide Capacitive Relative Humidity Sensor for Monitoring Anodically Bonded Hermetic Micropackages," Journal of Microelectromechanical Systems 10(2):197-204, Jun. 2001.

Ford, "The Effect of Humidity on the Calibration of Precision Air Capacitors," Proceedings of the IEE—Part III: Radio and Communication Engineering 96(39):13-16, Jan. 1949.

Hautefeuille et al., "A MEMS-based wireless multisensor module for environmental monitoring," Microelectronics Reliability 48:906-910, 2008.

Laconte et al., "High-Sensitivity Capacitive Humidity Sensor Using 3-Layer Patterned Polyimide Sensing Film," Proceedings of IEEE Sensors 1:372-377, 2003.

Hunter et al., "Smart Sensor Systems," The Electrochemical Society Interface, pp. 29-34, 2010.

* cited by examiner

TUNABLE HUMIDITY SENSOR WITH INTEGRATED HEATER

BACKGROUND

1. Technical Field

The present disclosure relates to the field of humidity sensors. The present disclosure relates in particular to a capacitive humidity sensor.

2. Description of the Related Art

Humidity sensing is important in many fields. In many applications it is beneficial to control the humidity level. In other applications it is beneficial simply to know what the humidity level is. In many manufacturing settings it is important that the relative humidity not rise above a certain level or the products being manufactured may be adversely affected. In many scientific settings the relative humidity is taken into account while performing experiments. When processing certain types of integrated circuits the humidity level may be closely monitored or controlled both in the clean room settings as well as in the various deposition chambers and processing equipment.

Humidity sensors come in a variety of forms. Humidity sensors can include resistive humidity sensors, thermal conduction humidity sensors, capacitive humidity sensors, and others. Humidity sensors can also be manufactured using thin film techniques. Thin film technology has reduced the size and cost of humidity sensors. However, humidity sensors with specific design requirements for particular applications may yet be very expensive.

BRIEF SUMMARY

One embodiment is a capacitive humidity sensor including a first electrode, a second electrode, and a humidity sensitive dielectric layer between the first and second electrodes. The humidity sensitive dielectric layer has uneven thickness between the first and second dielectric layers. The uneven thickness of the humidity sensitive dielectric layer leaves hollow portions between the first and second electrodes. An opening in the second electrode exposes the humidity sensitive dielectric layer to the environment surrounding the capacitive humidity sensor. Humid air in the environment enters into the humidity sensitive dielectric layer. The dielectric constant of the humidity sensitive dielectric layer changes as water vapor enters the humidity sensitive dielectric layer. As the dielectric constant of the humidity sensitive dielectric layer changes, the capacitance between the first and second electrodes changes. The capacitance of the first and second electrodes is therefore indicative of the humidity in the environment surrounding the capacitive humidity sensor.

In one embodiment the first electrode includes contact regions connected thereto. The contact regions are configured to pass a current through the first electrode. The current generates heat in the first electrode and heats the humidity sensitive dielectric layer to release humidity from the humidity sensitive dielectric layer.

One embodiment is a method for forming a capacitive humidity sensor. The method includes forming a first electrode on a substrate, forming a humidity sensitive dielectric layer on the first electrode, and forming a second electrode on the humidity sensitive dielectric layer. The method further includes forming openings in the second electrode and isotropically etching the humidity sensitive dielectric layer for a selected length of time. The isotropic etch removes portions of the humidity sensitive dielectric layer between the first and second electrodes leaving hollow spaces between the first and second electrodes. The longer the duration of the isotropic etch, the larger the hollow spaces between the first and second electrodes. The base capacitance between the first and second electrodes varies according to the ratio of the volume of the humidity sensitive dielectric layer to the volume of the hollow spaces between the first and second electrodes. The base capacitance of the capacitive humidity sensor can be selected by selecting a duration of the isotropic etch.

Humid air in the environment enters into the humidity sensitive dielectric layer through the openings in the second electrode. The dielectric constant of the humidity sensitive dielectric layer changes as water vapor enters the humidity sensitive dielectric layer. As the dielectric constant of the humidity sensitive dielectric layer changes, the capacitance between the first and second electrodes changes. The capacitance of the first and second electrodes is therefore indicative of the humidity in the environment surrounding the capacitive humidity sensor.

DETAILED DESCRIPTION

Figure 1:
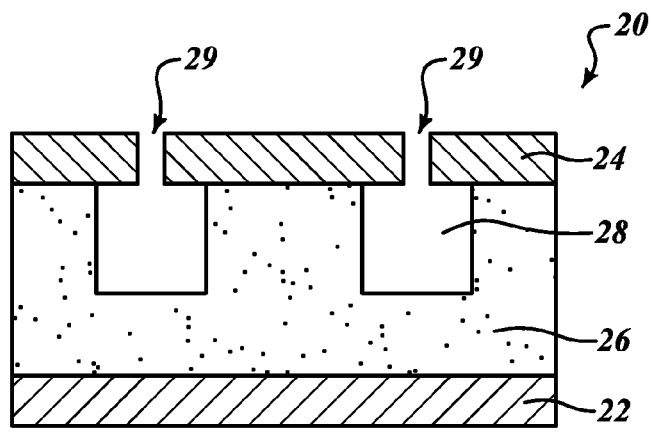
FIG. 1 is a cross section of a capacitive humidity sensor according to one embodiment.

FIG. 1 illustrates a capacitive humidity center 20 according to one embodiment. The capacitive humidity sensor 20 is a capacitor including a bottom electrode 22 and a top electrode 24. A humidity sensitive dielectric layer 26 is positioned between the bottom electrode 22 and the top electrode 24. Hollow spaces 28 are formed in the humidity sensitive dielectric layer 26. Portions of the hollow spaces 28 are positioned directly between the bottom electrode 22 and the top electrode 24. Openings 29 are formed in the top electrode 24.

The capacitive humidity sensor 20 outputs a capacitance signal indicative of the humidity in the surrounding environment. The capacitance of a capacitor varies according to the following relationship:

$$C \sim \epsilon \times A/d$$

where C is the capacitance, $\epsilon$ is the dielectric constant of the dielectric material between the electrodes of the capacitor, A is the area of overlap of the electrodes of the capacitor, and d is the distance between the electrodes of the capacitor. Thus, the capacitance of the capacitor is proportional to the dielectric constant $\epsilon$ of the dielectric material between the plates of the capacitor. The higher the dielectric constant of the dielectric material between the plates of the capacitor, the higher the capacitance of the capacitor will be.

Each dielectric material has a dielectric constant particular to that material. The dielectric constant of some materials changes according to environmental conditions. For example, some dielectric materials have a dielectric constant that changes with fluctuations in temperature, pressure, frequency of electric field, or humidity. Some capacitors have multiple dielectric materials between the two electrodes. The capacitance of such a capacitor will include components of capacitance from each dielectric material.

The capacitive humidity sensor 20 of FIG. 1 is a capacitor having a bottom plate 22 separated from top plate 24 by a combination of a humidity sensitive dielectric material 26 and air in the hollow pockets 28. The capacitor 20 has a lower capacitance than it would if the space between the bottom electrode 22 and top electrode 24 were filled completely by the dielectric material 26. This is because the dielectric constant of air is lower than the dielectric constant of the dielectric material 26.

The openings 29 in the top electrode 24 allow air from the environment surrounding the capacitive humidity sensor 20 to enter into the hollow regions 28 and to come into contact with the humidity sensitive dielectric layer 26. The humidity sensitive dielectric layer 26 absorbs water from the air. The dielectric constant of the humidity sensitive dielectric layer 26 increases as the humidity sensitive dielectric layer 26 absorbs humidity from the air. As the dielectric constant of the humidity sensitive dielectric layer 26 increases, the capacitance of the humidity sensitive capacitor 20 also increases. As the humidity of the air increases, the humidity sensitive dielectric material absorbs more moisture. Thus, by measuring the capacitance of the capacitive humidity sensor 20, a measurement of the humidity in the air surrounding the capacitive humidity sensor 20 can be obtained.

Because the total capacitance of the capacitive humidity sensor 20 depends on both the portion of capacitance contributed by the humidity sensitive dielectric layer 26 and the portion contributed by the air pockets 28, the range of capacitance of the capacitive humidity sensor 20 can be tuned by increasing or decreasing the size of the hollow pockets 28 between the top plate 24 and the bottom plate 22. If the volume of the hollow space 28 between the top plate 24 and the bottom plate 22 is greater, the capacitance of the capacitive humidity sensor 20 lowers. In some applications, it is desired to select a particular base capacitance value (capacitance value at 0% humidity) for the capacitive humidity sensor 20. The base capacitance of the capacitive humidity sensor 20 can be easily adjusted during manufacture of the capacitive humidity sensor 20 by forming a larger or a smaller hollow portion 28 between the bottom electrode 22 and the top electrode 24.

In one embodiment, the capacitive humidity sensor 20 is formed using thin film processes, such as those used in the formation of integrated circuits. In a thin film process for forming a capacitive humidity sensor 20, a first thin film conductive layer 22 is formed on an insulating substrate and the humidity sensitive dielectric layer 26 is deposited on the first thin film conductive layer. A second thin film conductive layer 24 is then formed on top of the humidity sensitive dielectric layer 26. Openings 29 are formed in the second conductive thin film layer 24.

The humidity sensitive dielectric layer 26 is then etched through the holes 29. If the etch is isotropic, it removes the humidity sensitive dielectric layer 26 both in the vertical direction below the holes 29 and laterally between the thin film metal layers 22, 24. If the etch is anisotropic, the etch will be vertical and have the same width as the openings 29. Usually, an isotropic etch is preferred since this will have a much greater effect on changes in the dielectric constant of the material 26. The amount of material removed from the humidity sensitive dielectric layer 26 directly between the first and second conductive films 22, 24 will affect the capacitance of the capacitive humidity sensor 20. Thus, after forming openings 29 in the second conductive thin film 24, the capacitance of the capacitive humidity sensor 20 can be selected by selecting a particular amount of material to etch of the humidity sensitive dielectric layer 26. For a particular etch chemistry, a longer duration of the etch will etch more of the humidity sensitive dielectric layer 26 between the top electrode 24 and the bottom electrode 22. A shorter etch will etch less of the humidity sensitive dielectric layer 26 between the top electrode 24 and the bottom electrode 22. Alternatively, etch parameters other than etch duration may be varied in order to select a particular capacitance value of the capacitor. For example the pressure in the deposition chamber, flow rates of gasses in the deposition chamber, temperature in the deposition chamber, etch chemistry, or other parameters can each be varied to select a particular target value of the capacitance of the capacitive humidity sensor 20.

In one embodiment, the humidity sensitive dielectric layer 26 is polyimide. The dielectric constant of polyimide varies from about 2.9 at 0% humidity to about 3.4 at 100% humidity. Other suitable humidity sensitive dielectric layers may be used in forming the capacitive humidity sensor 20. A humidity sensitive material with respect to this application refers to a material whose dielectric constant varies with variations in the humidity.

When making successive humidity measurements, if the humidity decreases there is a time lag between when the humidity goes down and the water leaves the dielectric 26. In some conditions, it may take some time for the water content absorbed by the humidity sensitive dielectric layer 26 to leave the humidity sensitive dielectric layer 26. Thus, it is possible that a measurement of the humidity may be erroneously high because humidity has been previously absorbed by the humidity sensitive dielectric layer 26 and has not yet left. The humidity in the air surrounding the capacitive humidity sensor 20 may have dropped while the dielectric constant of the humidity sensitive dielectric layer 26 has not yet dropped correspondingly because water content that was previously absorbed has not yet been expelled. In addition to this, hysteretic effects may occur in measurements of the capacitance of the capacitive humidity sensor 20. In other words, as the humidity sensitive dielectric layer 26 absorbs moisture from the air, the dielectric constant will increase along a first curve. But as the humidity decreases, the dielectric constant of the humidity sensitive dielectric layer 26 does not decrease along the same curve. Therefore, it is possible for the capacitive humidity sensor 20 to give two different readings for the same actual humidity level in the environment surrounding the capacitive humidity sensor 20. For this reason, it is desirable to be able to quickly expel moisture content from the humidity sensitive dielectric layer 26 after each reading of the capacitance of the capacitive humidity sensor 20.

Therefore, in one embodiment, the bottom electrode 22 is also a heating element. The bottom electrode 22 is configured to generate heat and to heat up the humidity sensitive dielectric layer 26. When the humidity sensitive dielectric layer 26 is heated up, moisture content is expelled from the humidity sensitive dielectric layer 26. A subsequent measurement of humidity will not be erroneously affected by either hysteresis or by an unduly high portion of moisture remaining in the humidity sensitive dielectric layer 26. In one embodiment, a current is passed through the bottom electrode 22. The current causes the bottom electrode 22 to generate heat and to heat up the humidity sensitive dielectric layer 26 and to expel moisture content from the humidity sensitive dielectric layer 26.

While particular materials, heating elements, structures and processes have been described for forming a capacitive humidity sensor 20, many other particular structures, processes and materials can be used in accordance with principles of the present disclosure. All such materials, processes and structures fall within the scope of the present disclosure.

Figure 2:
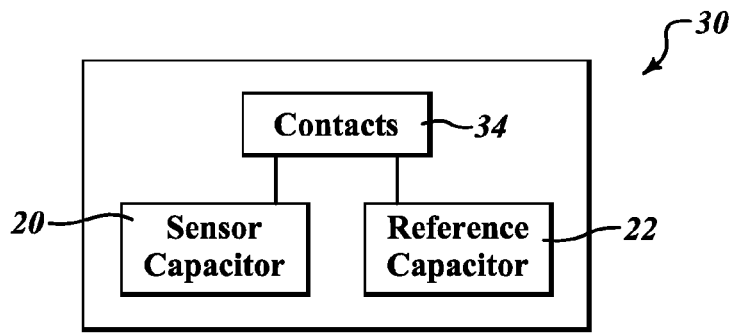
FIG. 2 is a block diagram of an electronic device according to one embodiment.

FIG. 2 illustrates an electronic device 30 according to one embodiment. The electronic device 30 includes a sensor capacitor 20, which is a capacitive humidity sensor 20 as described in relation to FIG. 1; a reference capacitor 32 and electrical contacts 34. The sensor capacitor 20 senses humidity in the air surrounding the electronic device 30 and provides a capacitance signal indicative of the humidity in the air surrounding the electronic device 30. The reference capacitor 32 is a capacitor similar to the sensor capacitor 20 except that the dielectric layer is not exposed to open air. The capacitance is therefore a constant and does not change with humidity. In one embodiment, hollow portions 28 are not formed in the humidity sensitive dielectric layer 26. Openings 29 are also not formed in the humidity sensitive dielectric layer 26 of the reference capacitor 32.

The capacitance of the reference capacitor 32 is independent of humidity. The control capacitive signal is independent of the humidity because openings 29 have not been formed in the reference capacitor 32, and is otherwise sealed to block ambient air from coming in contact with the humidity sensitive dielectric material 26. The reference capacitor 32 therefore gives a constant control capacitance signal.

Electrical contacts 34 are connected to the sensor capacitor 20 and the reference capacitor 32. The electrical contacts 34 receive the capacitive signals from the sensor capacitor 20 and the reference capacitor 32 and outputs them to processing circuitry which can be connected to the electrical device 30. The processing circuitry is not shown in FIG. 2 for simplicity.

In one embodiment, the electronic device 30 is a standalone integrated circuit package. The sensor capacitor 20, the reference capacitor 32, and the electrical contacts 34 are formed on an integrated circuit die. The electrical contacts 34 can include contact pads on top of an integrated circuit die, solder balls connected to the integrated circuit package 30, leads of a lead frame, pins of a pin grid array, or any other suitable electrical contacts. The integrated circuit package 30, including the sensor capacitor 20, can be conveniently installed in an electrical system which can process the capacitance signals generated by the sensor capacitor 20 and the reference capacitor 32 and output a measurement of the humidity of the air surrounding the integrated circuit package 30.

Figure 3:
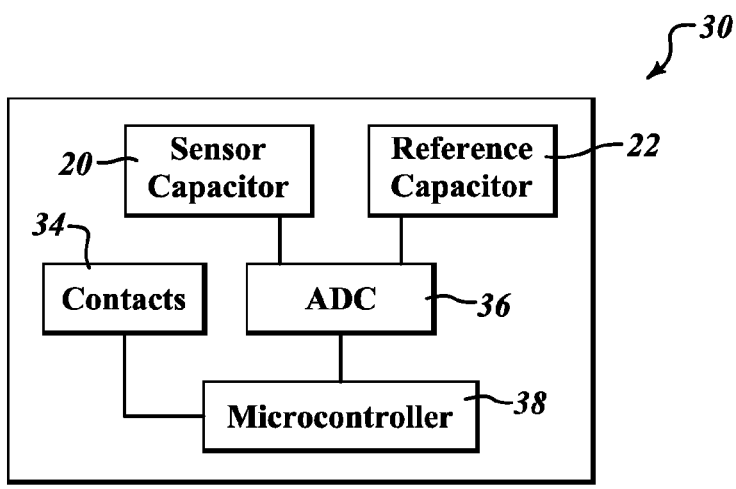
FIG. 3 is a block diagram of an electronic device according to an alternative embodiment.

FIG. 3 is a block diagram of an electronic device according to one embodiment. The electronic device 30 includes a sensor capacitor 20, a reference capacitor 32, an analog-to-digital converter 36, and a microcontroller 38. The sensor capacitor 20 and the reference capacitor 32 each are coupled to the analog-to-digital converter 36. The sensor capacitor 20 outputs an analog humidity signal indicative of the humidity in the environment surrounding the electronic device 30. The analog-to-digital converter 36 receives the analog humidity signal from the sensor capacitor 20 and converts the analog humidity signal to a digital humidity signal. The analog-to-digital converter 36 outputs the digital humidity signal to the microcontroller 38. The microcontroller 38 receives the digital humidity signal from the analog-to-digital converter 36 and computes a value of the humidity in the environment surrounding the electronic device 30. The microcontroller 38 references a calibration table stored in memory in the microcontroller 38 when computing the value of the humidity. The microcontroller 38 may compare the digital humidity to values stored in the calibration table and compute, calculate, or estimate a value of the humidity signal based on the digital humidity signal and the value stored in the calibration table.

The reference capacitor 32 also outputs an analog reference signal to the analog-to-digital converter 36. The analog reference signal is a reference capacitance signal from the reference capacitor 32. The analog-to-digital converter 36 converts the analog reference capacitor signal to a digital reference capacitor signal and outputs the digital reference capacitor signal to the microcontroller 38.

The capacitance of the capacitive humidity sensor 20 can be affected by factors other than humidity. The temperature, pressure, or other factors can each affect the capacitance of the capacitive humidity sensor 20. The reference capacitor 32 helps to maintain accuracy in estimating the humidity based on the capacitive humidity sensor 20. The capacitance of the reference capacitor is also affected by temperature, pressure, and factors other than humidity. Therefore if the reference capacitor has a higher or lower value than expected, the final humidity measurement can take into account that the capacitance of the capacitive humidity sensor 20 may be higher or lower than can be accounted for based on humidity alone.

The microcontroller 38 references the digital control signal when computing the value of the humidity from the digital humidity signal. In one embodiment, the digital control capacitor signal acts as a base reference signal for the microcontroller 38. The microcontroller 38 can store in the calibration table values of the digital control capacitor signal. The microcontroller 38 can then take into account the value of digital control capacitor signal or fluctuations in that signal when calculating the value of the humidity from the digital humidity signal. The microcontroller 38 can then output the value of the humidity through the electrical contacts 34 to a display device or any other peripheral device coupled to the electronic device 30. The microcontroller 38 can also receive input commands and requests as well as supply voltages through the contacts 34. In some embodiments, the value of the humidity is used by other circuits on the same electronic device 30. In those cases, the signal is sent to other locations on the device 30 and does not need to leave through contacts 34.

In one embodiment, the electronic device 30 is an integrated circuit package. The integrated circuit package includes an integrated circuit die in which is formed the sensor capacitor 20, the reference capacitor 32, analog-to-digital converter 36, and the microcontroller 38. The analog-to-digital converter 36 and the microcontroller 38 can be formed from transistors formed in the integrated circuit die. The transistors can be formed from a monocrystalline semiconductor substrate in the integrated circuit die as well as through metal interconnection layers and dielectric layers in the integrated circuit die. The sensor capacitor 20 and the reference capacitor 32 can be formed in an upper portion of the integrated circuit die above the semiconductor substrate. Openings can be made in the integrated circuit die to expose the sensor capacitor 20 to the air surrounding the integrated circuit package 30. The electrical contacts 34 can be contact pads, leads of a lead frame, solder balls, pins of a pin grid array, or any other suitable electrical contacts. Further details regarding the formation of an integrated circuit package including a capacitive humidity sensor, microcontroller, and analog to digital converter can be found in U.S. patent application Ser. Nos. 13/285,911, 13/285,894, 13/285,867, all of which are incorporated by reference herein in their entirety. While specific components and connections have been described in relation to FIG. 3, many other specific configurations including computation schemes, conversion schemes, analog signals, and digital signals can be used without departing from the scope of the present disclosure. Many circuits for comparing the value of two capacitors to each other and outputting a signal based on this difference are well known in the art today and any of these are acceptable for use in the sensing circuit herein. For example, in one embodiment, the sensor capacitor 20 and the reference capacitor 22 are coupled to a comparator circuit that outputs a single signal indicating the difference in capacitor values between the two. This single signal can then be used as corresponding to the humidity value. In this embodiment, the comparator circuit is directly coupled to the capacitors 20 and 23 prior to the A to D converter.

Figure 4A:
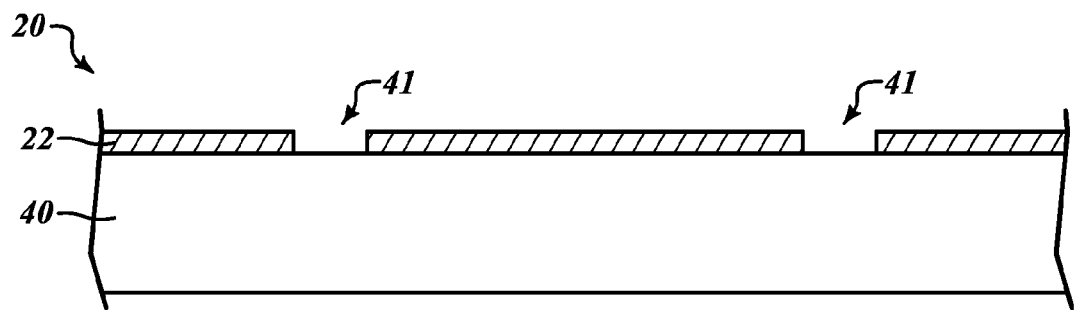
FIG. 4A is a cross section of a capacitive humidity sensor at an intermediate stage of manufacture according to one embodiment.

FIG. 4A illustrates a capacitive humidity sensor 20 at an intermediate stage of processing. A thin film layer 22 of a conductive material is formed on the dielectric substrate 40. The thin film layer 22 is the bottom electrode of the capacitive humidity sensor 20. The bottom electrode 22 is patterned and etched to form openings 41 exposing portions of the dielectric substrate 40.

The dielectric substrate 40 is, in one example, a layer of silicon dioxide about 1 μm thick. The bottom electrode 22 is, in one example, a tantalum aluminum layer about 800 Å thick. The tantalum aluminum layer 22 can be deposited by a physical vapor deposition process, such as sputtering, or by any other suitable process for deposing a thin film of conductive material. The dielectric substrate 40 may be formed on a semiconductor substrate (not shown). The semiconductor substrate may include transistors. The dielectric substrate 40 may include metal interconnections connected to the transistors that are part of analog to digital converter 36, and microcontroller 38.

Figure 4B:
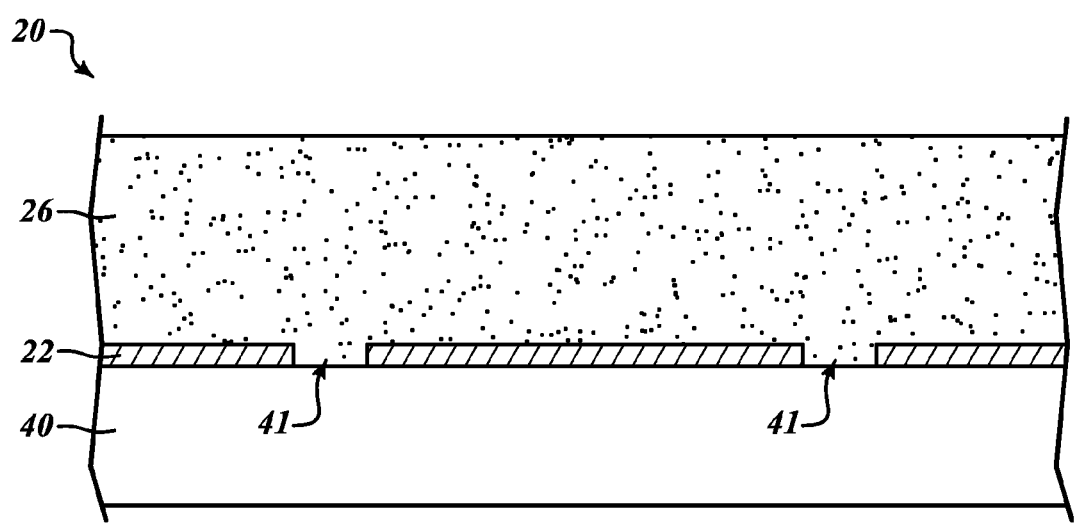
FIG. 4B illustrates the capacitive humidity sensor of FIG. 4A with a humidity sensitive dielectric formed on a bottom electrode according to one embodiment.

In FIG. 4B, a humidity sensitive dielectric layer 26 is formed on the bottom electrode 22 and contacts the exposed portions of the dielectric substrate 40. The humidity sensitive dielectric layer 26 has a dielectric constant which changes according to moisture content absorbed by the humidity sensitive dielectric layer 26. In one example, the humidity sensitive dielectric layer 26 is a layer of polyimide about 8 μm thick. Polyimide adheres poorly to the tantalum aluminum of the bottom electrode 22. This is one reason openings 41 are formed in the bottom electrode 22, to expose the dielectric substrate 40. The polyimide 26 contacts the silicon dioxide of the dielectric substrate 40 and adheres relatively strongly with the dielectric substrate 40. The openings 41 and the bottom electrode 22 are between 5 and 10 μm across and may be round, square or other shape. The polyimide layer 26 is deposited by a chemical vapor deposition process. The polyimide layer 26 can also be formed by any other suitable process. Such processes for forming polyimide layers are well known to those of skill in the art and all such suitable processes fall within the scope of the present disclosure. In one embodiment the etched polyimide layer 26 has a dielectric constant that is about 2.9 at 0% humidity and about 3.4 at 100% humidity. Different types of polyimide may be used having lower or higher dielectric constants than described herein.

Alternatively, the humidity sensitive dielectric layer 26 may be a material other than polyimide. Any suitable humidity sensitive dielectric material may be used. All such suitable humidity sensitive dielectric materials fall within the scope of the present disclosure. In some cases, the adherence openings 41 are not necessary if the dielectric 26 has sufficient adherence to the electrode 22.

Figure 4C:
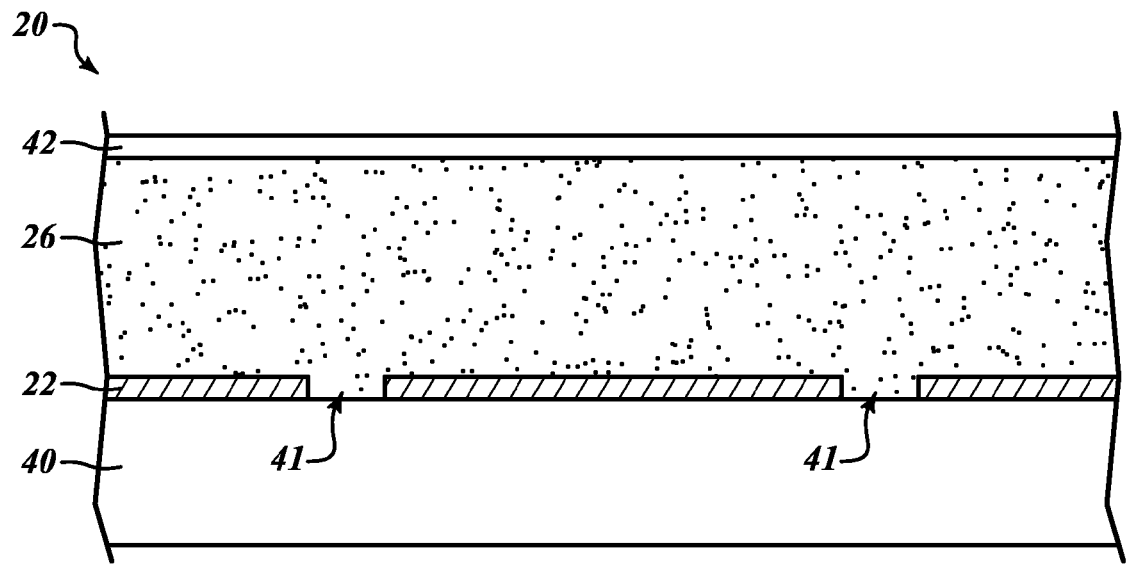
FIG. 4C illustrates the capacitive humidity sensor of FIG. 4B with a passivation layer on the humidity sensitive dielectric according to one embodiment.

As shown in FIG. 4C, a dielectric layer 42 is deposited on the humidity sensitive dielectric layer 26. The dielectric layer 42 is, for example, a layer of phosphosilicate glass about 5,000 Å thick. Alternatively, the dielectric layer 42 can be any other suitable dielectric layer, such as silicon dioxide, silicon nitride, or any other suitable dielectric material.

Figure 4D:
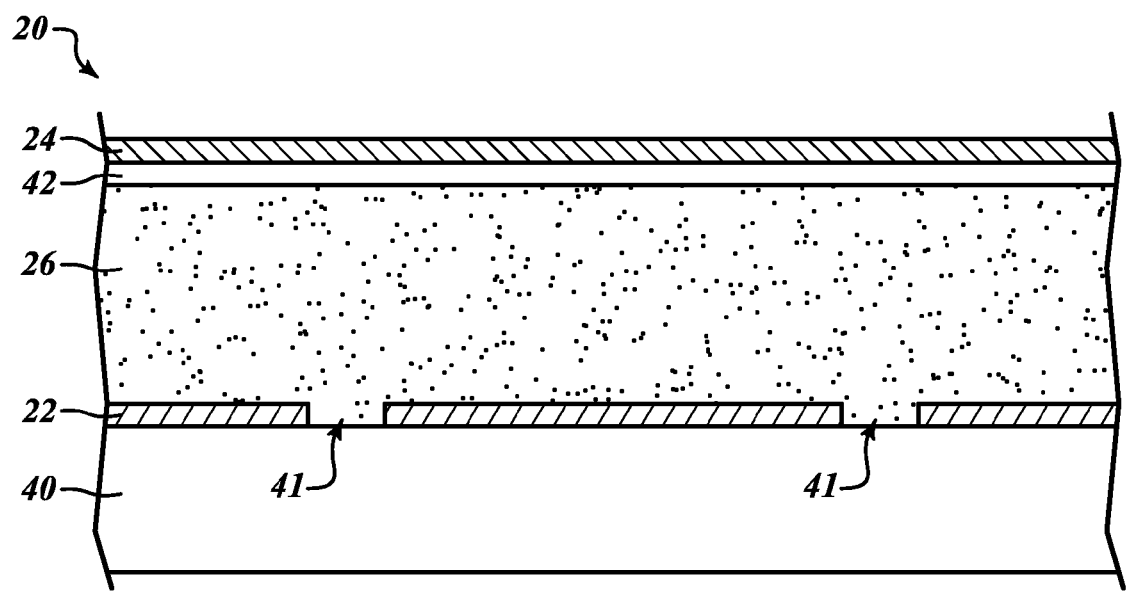
FIG. 4D illustrates the capacitive humidity sensor of FIG. 4C with a top electrode formed on the passivation layer according to one embodiment.

As shown in FIG. 4D, a thin film conducting layer 24 is deposited on the dielectric layer 42. The thin film conducting layer 24 is the top electrode of capacitive humidity sensor 20. The top electrode 24 is, in one example, an aluminum layer about 5,000 Å thick on a barrier layer of titanium tungsten about 1,000 Å thick. Alternatively, other suitable conductive materials and barrier layers may be used in place of aluminum or titanium tungsten. All such suitable conductive materials fall within the scope of the present disclosure.

Figure 4E:
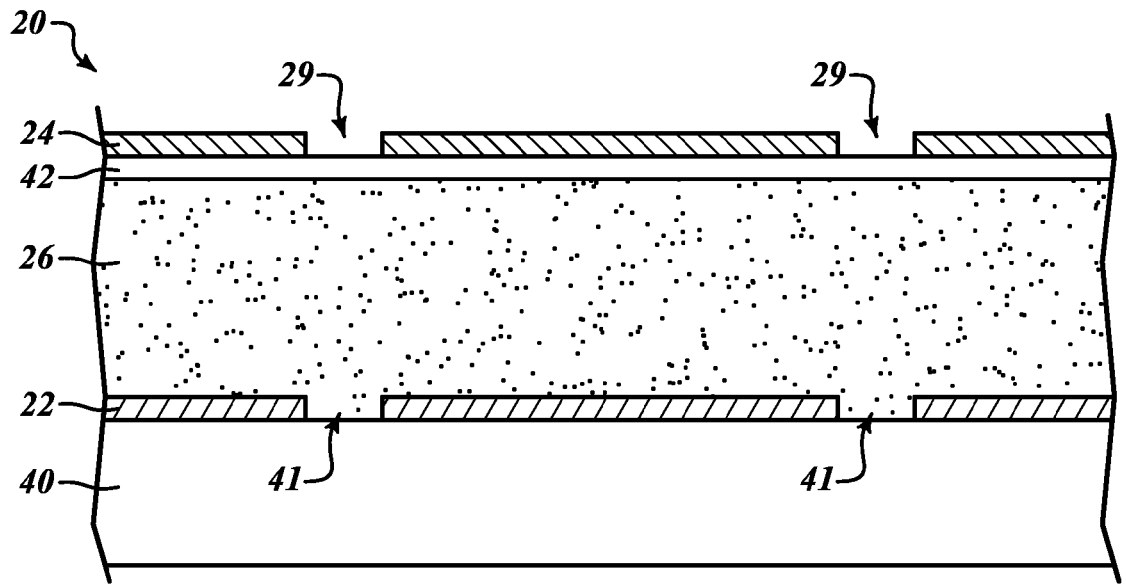
FIG. 4E illustrates the capacitive humidity sensor of FIG. 4D with openings formed in the top electrode according to one embodiment.
Figure 4F:
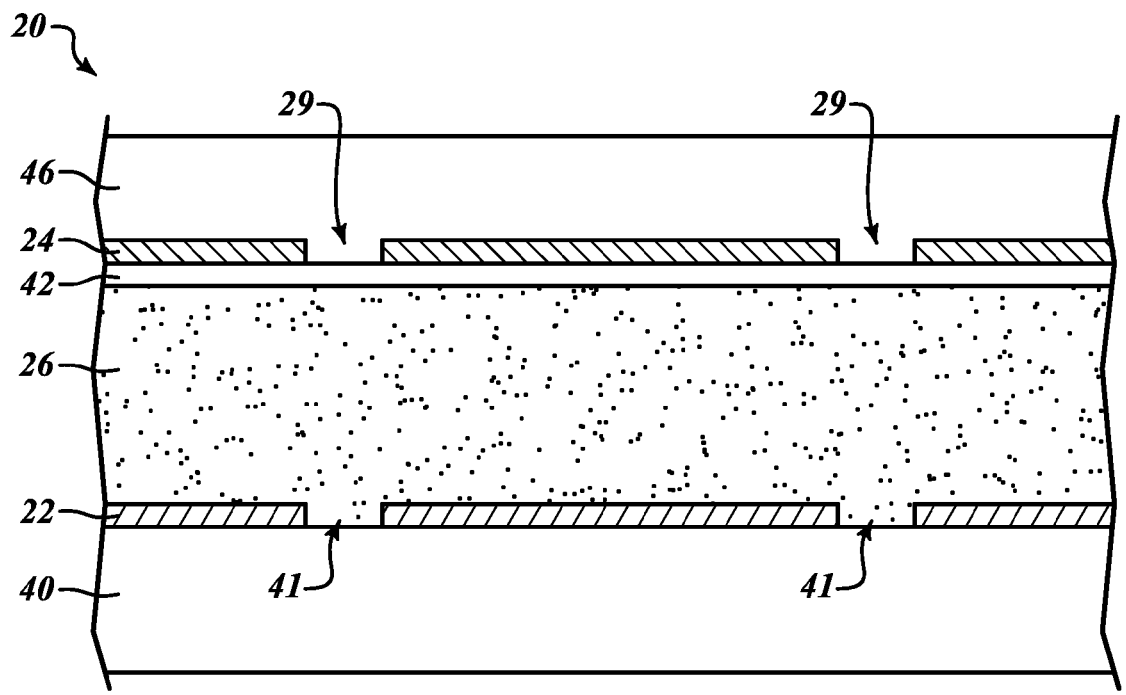
FIG. 4F illustrates the capacitive humidity sensor of FIG. 4E with a passivation layer on the top electrode according to one embodiment.

As shown in FIG. 4E, the top electrode 24 is patterned and etched to form openings 29 exposing the dielectric layer 42. The openings 29 are formed directly above the openings 41 in the bottom electrode 22 in one embodiment. The area A of the capacitor 20 formed by the top plate 24, the bottom plate 22, and the dielectric layers 42, 26 between the top and bottom plates 24, 22 is determined in part by the overlapping area of the top electrode 24 and the bottom electrode 22. The openings 29, 41 which have been etched in the top electrode 24 and the bottom electrode 22 do not contribute to the capacitance of the capacitor 20. Therefore, it is advantageous that holes 29 formed in the top electrode 24 be aligned with holes 41 formed in the bottom electrode 22. The openings 29 in the top electrode 24 are approximately the same size as the openings 41 in the bottom electrode 22. The openings 29 are, therefore, about 5 to 10 μm across in one embodiment. Alternatively, it may be advantageous to form the openings 41 slightly larger than the openings 29 to allow for some misalignment between the masks used to form the openings 41 and the openings 29.

In one embodiment, few if any of the openings 29 will actually be in alignment with the apertures 41. Rather, in one embodiment, the apertures 29 will be over to the electrode surface as shown in FIG. 1 and not over the openings 41.

Figure 4G:
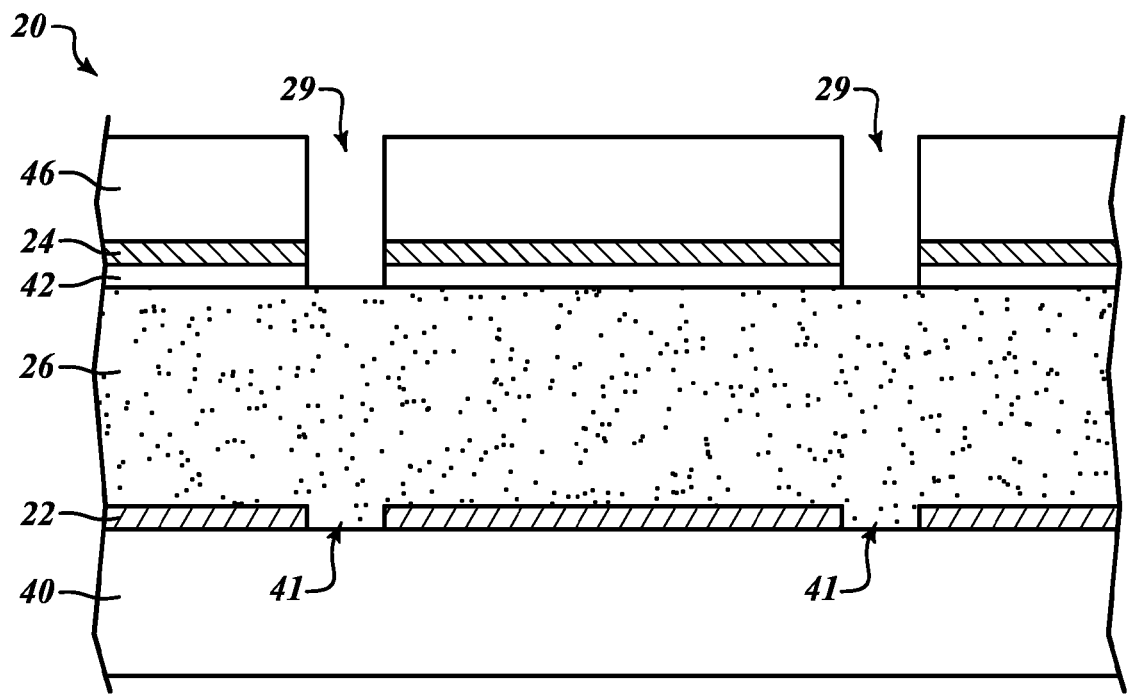
FIG. 4G illustrates the capacitive humidity sensor of FIG. 4F with openings formed in the passivation layer and the passivation layer according to one embodiment.

As shown in FIG. 4G, a dielectric layer 46 is formed on the top electrode 24 and on exposed portions of the dielectric 42. The dielectric 46 is, in one example, a layer of phosphosilicate glass about 1 μm thick. The phosphosilicate glass 46 acts as a passivation layer for the capacitive humidity sensor 20. The dielectric layer 46 and the dielectric layer 42 are anisotropically etched to expose portions of the humidity sensitive dielectric layer 26. The dielectric 46 and the dielectric 42 can be etched by any suitable process, including dry etches or wet etches performed for suitable lengths of time.

Figure 4H:
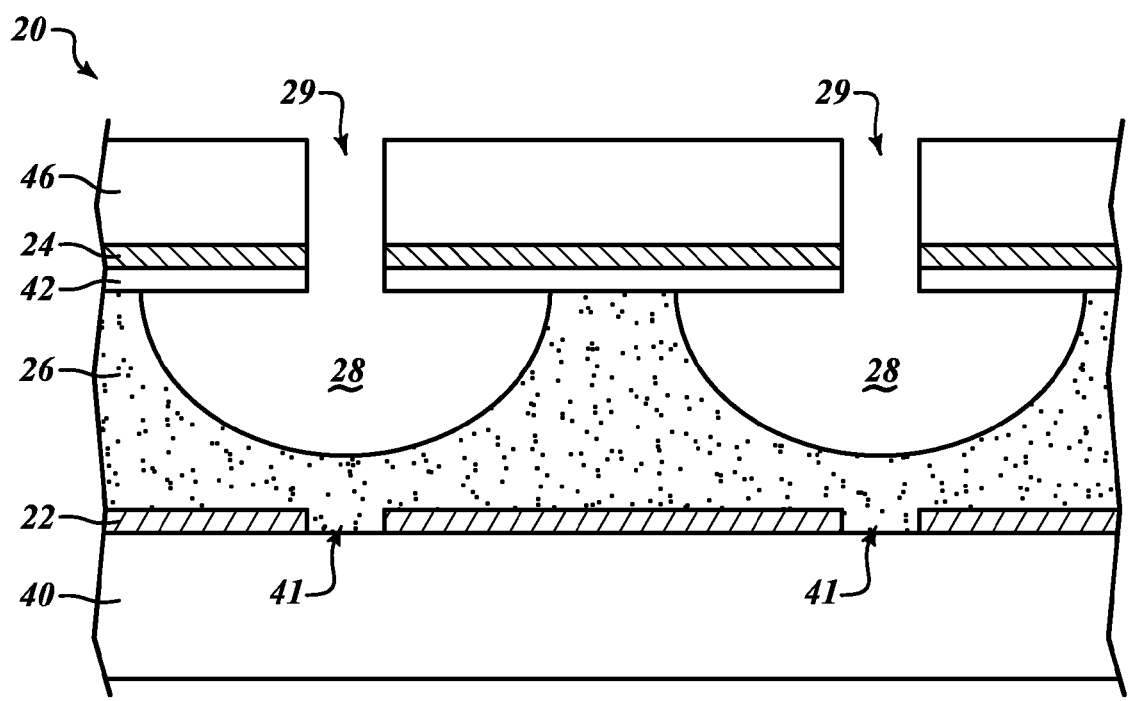
FIG. 4H illustrates the capacitive humidity sensor of FIG. 4G with hollow portions formed in the humidity sensitive dielectric according to one embodiment.

As shown in FIG. 4H, the humidity sensitive dielectric layer 26 is isotropically etched through the openings 29. Because the humidity sensitive dielectric layer 26 is isotropically etched, hollow portions 28 are formed between the top electrode 24 and the bottom electrode 22. The isotropic etch leaves a substantially semicircular cross-section of the hollow portions 28. The capacitance of the capacitor 20 in FIG. 4H is lower than the capacitance of the capacitor 20 in FIG. 4G. This is because the humidity sensitive dielectric layer 26 has been replaced by air to some extent between the bottom electrode 22 and the top electrode 24. The dielectric constant of air is 1 and is lower than the dielectric constant of humidity sensitive dielectric layer 26. Therefore, the larger the volume of air between the top electrode 24 and the bottom electrode 22 the smaller the capacitance of the capacitor 20.

The humidity sensitive dielectric layer 26 can be isotropically etched by a dry plasma etch. The dry plasma etch can be supplemented by a reactive ion etch as well. The duration of the plasma etch, the pressure of the plasma etch, and the temperature at which the plasma etch is performed all affect the extent to which the polyimide 26 is removed. The value of the capacitance of the capacitor 20 can be selected by simply varying the time, pressure, or temperature of the plasma etch which isotropically etches the polyimide 26. A manufacturer of the capacitive humidity sensor 20 can, therefore, provide a capacitive humidity sensor 20 which has a capacitance custom selected by a customer with little to no extra cost because no new masks or layers have been deposited, only one or more etch parameters have been altered. In one embodiment, the etch which anisotropically etches the dielectric layers 46, 42, isotropically etches the humidity sensitive dielectric layer 26. Alternatively, the humidity sensitive dielectric layer 26 is etched in a separate etch from the etch which anisotropically etches the dielectric layers 46, 42.

Because the humidity sensitive dielectric layer 26 is exposed to air through openings 29, the humidity sensitive dielectric layer 26 can absorb moisture from the air. The dielectric constant of the humidity sensitive dielectric layer 26 changes according to an amount of moisture absorbed from the air. A measurement of the capacitance of the capacitor 20 gives an indication of the humidity content in the air. Pure polyimide has a dielectric constant in the range of about 3.2. Pure water has a dielectric constant in the range of 80. Therefore, when even small amounts of water are absorbed by the dielectric polyimide, the change is measurable.

A capacitive humidity sensor 20 which includes both air and polyimide as the dielectric between electrodes provides better precision in the spectrum of 70% to 100% relatively humidity. A capacitive humidity sensor 20 which includes only polyimide between the top electrode 24 and the top electrode 22 has a capacitance which varies with a relatively small slope throughout the range from 0% to 100% relatively humidity. However, a capacitive humidity sensor 20 which includes a combination of air and a humidity sensitive dielectric layer 26 has an increased, almost exponential slope in the range between 70% and 100% relative humidity.

One preferred method to tune the sensitive region of the polyimide is to control the size of the hollow regions 28 and the amount of undercut below electrode 42. With little to no undercut, the sensor has more sensitivity in the humidity range of 20% to 60%, while with a large undercut, remaining over 50% of the polyimide, the greatest sensitivity is in the range of 70% to 100% humidity. The sweet spot for sensitivity can therefore be tuned based on the depth of the etch and the amount of material removed. The present humidity sensor is therefore beneficial since the sensitivity can be tuned easily and at low cost, with no additional masks.

The capacitive humidity sensor 20 of FIG. 4H is also highly sensitive to charge variations between the two plates. This allows sub-pF capacitance changes to be measured accurately. Because sub-pF capacitances can be measured accurately, the size of the capacitive humidity sensor 20 can be very small. The capacitor 20 can be small enough to have a capacitance about 2 pF. While particular materials for the bottom and top electrodes 22, 24, the humidity sensitive dielectric layer 26, and the dielectric layers 42, 46 have been described herein, any suitable materials can be used in accordance with principles of the present disclosure. While specific thicknesses of the various layers and widths of the openings have been described, any suitable thicknesses and widths can be used according to principles of the present disclosure. While particular structures and sequences of etching have been described, any suitable structures and etches can be used in accordance with principles of the present disclosure.

Figure 5:
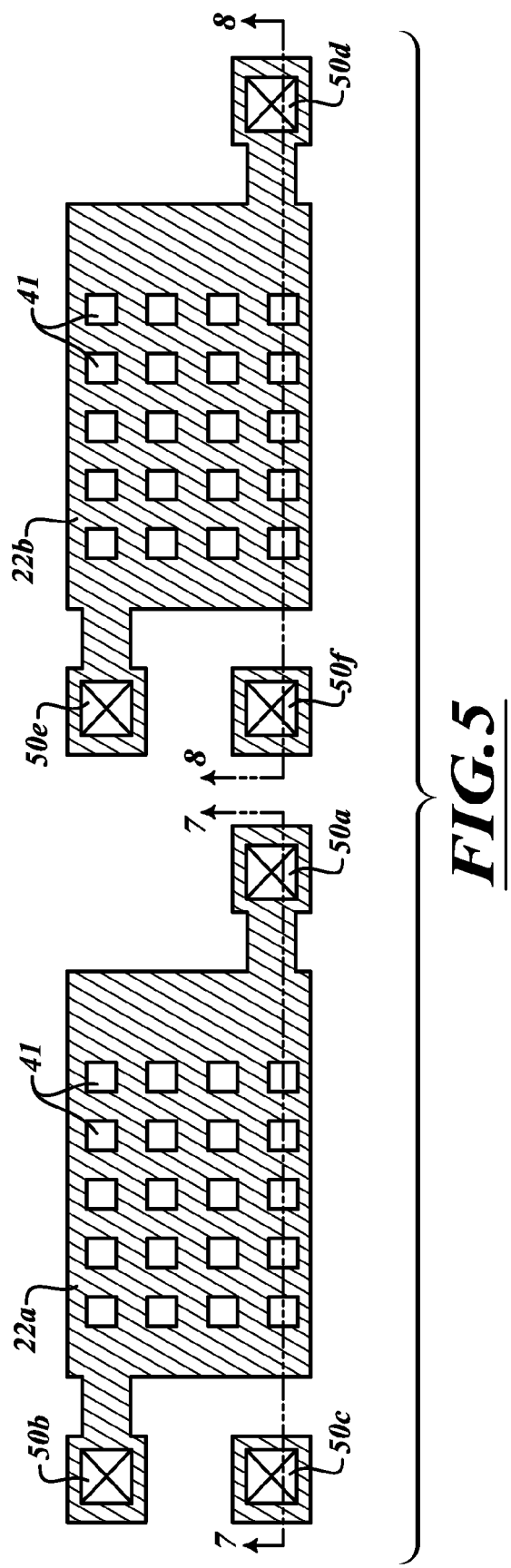
FIG. 5 is a top view of a bottom electrode of a capacitive humidity sensor according to one embodiment.

FIG. 5 is a top view of the bottom plate 22a of the sensor capacitor 20 and the bottom plate 22b of the reference capacitor 32 described previously. The bottom plates 22a, 22b are formed of the same metal layer. The metal layer is deposited over the dielectric substrate 40 (not shown) and patterned and etched to form the bottom electrodes 22a, 22b. The bottom electrodes 22a, 22b are, for example, titanium aluminum. In one embodiment, the bottom electrode 22a is identical to the bottom electrode 22b. Because the bottom electrode 22b is the bottom electrode of the reference capacitor 32, it is desirable that the reference capacitor 32 be identical to the sensor capacitor 20 in all ways except that it is not exposed to humidity and there are no air pockets 28 in the reference capacitor 32. The bottom electrode 22a has contact areas 50a, 50b. The contact areas 50a, 50b contact metal vias described further herein. As described previously, the bottom electrode 22a can act as a heating element to release moisture content from the humidity sensitive dielectric layer 26. A voltage can be applied across the contact areas 50a, 50b to pass a current through the bottom electrode 22a of the sensor capacitor 20. When the current passes through the bottom electrode 22a of the sensor capacitor 20, the bottom electrode 22a generates heat and heats the humidity sensitive dielectric layer 26 above the bottom electrode 22a. When the humidity sensitive dielectric layer 26 is heated, the moisture content absorbed therein is quickly released. When the moisture content of the humidity sensitive dielectric layer 26 has been released, after a reset time period in which it returns to ambient temperature, a subsequent measurement of the capacitance of the capacitor 20 can be performed and provide a more accurate indication of the humidity of the air in the environment.

In one embodiment, the bottom electrode 22 is selected for its electrical properties and ease of manufacture, such as polysilicon, or an alloy with small amounts of Cu and Si. A separate material, selected for its heating properties, is under the electrode 22. In this embodiment, the electrode 22 acts only as a plate of capacitor and a heater under the plate 22. The heater is coupled to a high current source and can rapidly be heated to a high temperature. Since the capacitor plate 22 is made of thermally conductive material, such as aluminum or polysilicon, and the heater is under it. The heat transfers easily to the polyimide 26.

By providing a separate heater layer under the electrode 22, each of these can be constructed to perform its desired function, heating and as an electrode, respectively, thus improving the properties of each and the overall operation of the circuit. For example, if a separate, specialized heater is used, it can achieve a higher temperature, with less current, more rapidly than if use of the electrode 22 as both the heater and as the electrode.

In some embodiments, there is a thin, dielectric insulator between the heater and the server electrode to ensure they are fully electrically isolated, while in other, they are in direct electrical contact with each other and the electrode 22 is disabled for use as a capacitor plate while the heater is functioning.

Contact region 50c is formed of the same metal layer as the bottom electrodes 22a, 22b, but is electrically isolated from the electrodes 22a, 22b. The contact region 50c is in electrical contact with the top layer 24 described layer herein. The bottom electrode 22b of the reference capacitor 32 includes contact regions 50d, 50e. Contact region 50f is formed of the same metal layer as the bottom electrodes 22a, 22b, but is electrically isolated from the electrodes 22a, 22b. As the humidity sensitive dielectric layer 26 in the reference capacitive humidity sensor 20 will absorb no moisture from the air, there is no need to pass a current between contacts 50d, 50e.

Figure 6:
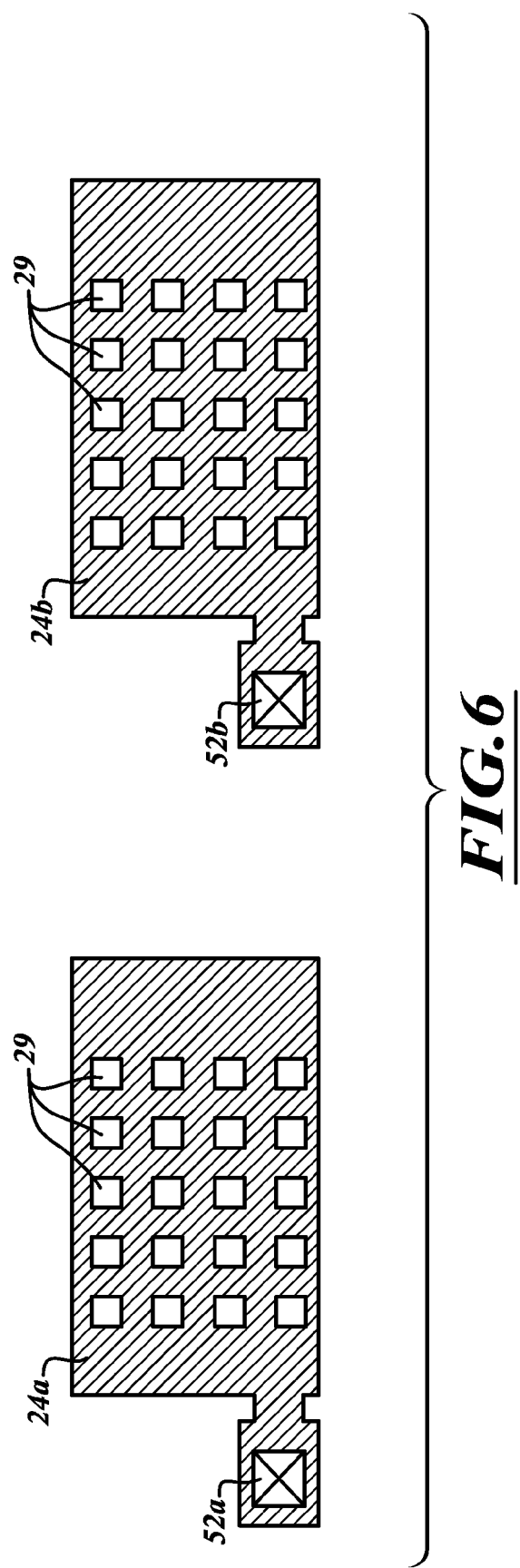
FIG. 6 is a top view of a top electrode of a capacitive humidity sensor according to one embodiment.

FIG. 6 is a top view of the top electrode 24a of the sensor capacitor 20 and the top electrode 24b of the reference capacitor 32. The top electrodes 24a, 24b are formed of the same metal layer. The metal layer is deposited on the dielectric layer 42, is patterned and etched to leave top electrodes 24a, 24b as shown in FIG. 6. Top electrode 24a of the sensor capacitor 20 includes contact region 52a. Contact region 52a is in electrical contact with metal vias which allow for signals to be read from the top electrode 24a. Contact region 52b is in contact with a metal via and allows signals to be read from the top electrode 24b of the reference capacitor 32.

Figure 7:
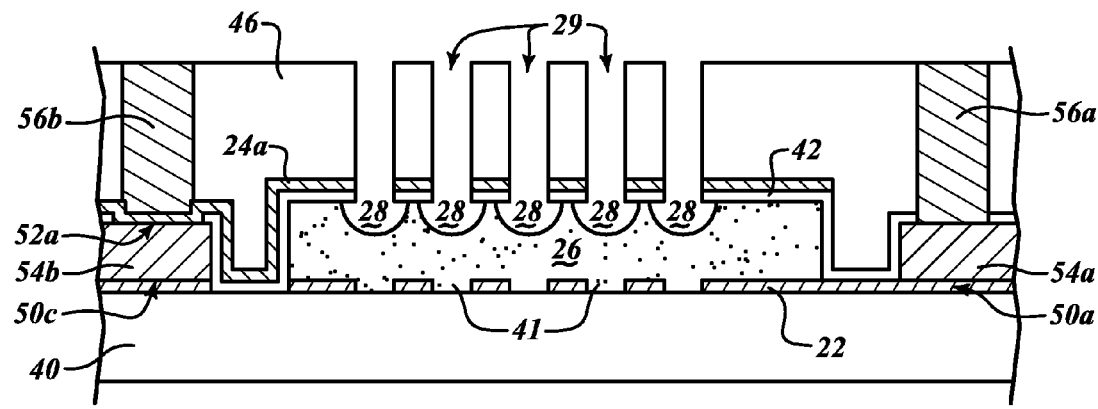
FIG. 7 is a cross section of the capacitive humidity sensor of FIG. 5 taken along lines 7-7 according to one embodiment.

FIG. 7 is a cross-section of the sensor capacitor 20 taken along cross-section lines 7 of FIG. 5. In FIG. 7, the bottom electrode 22a of the sensor capacitor 20 overlies the dielectric layer 40, as described previously (or in the alternative embodiment, overlies a separate heater). The bottom electrode 22a has been patterned and etched to form openings 41 which expose portions of the dielectric substrate 40. Contact region 50a is a region at which the bottom electrode 22a electrically contacts metal track 54a. Metal track 54a is electrically connected to via 56a. At contact region 50b, metal from the metal layer that was used to form the bottom electrode 22a contacts the metal track 54b. At contact region 50a, metal track 54b contacts the top electrode 24a of the sensor capacitor 20. The top electrode 24a is in electrical contact with via 56b. Metal tracks 54a, 54b are, for example, aluminum copper alloy metal tracks about 5,000 Å thick. The metal tracks 54a, 54b comprise about 98% aluminum and about 2% copper. Other alloys and compositions can be used to form metal tracks 54a, 54b in accordance with principles of the present invention. Vias 56a, 56b are also formed of aluminum copper alloy. The vias 56a, 56b allow electrical contact to be made to the bottom plate 22a and the top plate 24a from the top of the capacitive humidity sensor 20. Contact pads 34 may be formed on top of the metal vias 56a, 56b.

As described previously, air may enter through openings 29 to contact the humidity sensitive dielectric layer 26. The humidity sensitive dielectric layer 26 absorbs moisture from the air and the dielectric constant thereof changes. The capacitance of the sensor capacitor 20 changes as the dielectric constant of the humidity sensitive dielectric layer 26 changes. Also, the capacitance between the bottom electrode 22a and the top electrode 24a is based, in part, by the amount of air between the electrodes 24a, 22a. Other shapes, structures, and materials can be used in accordance with principles of the present disclosure.

Figure 8:
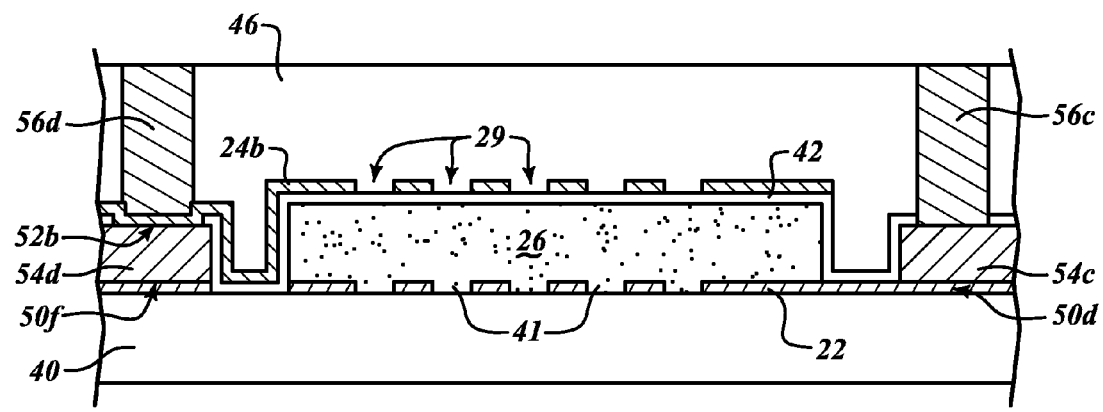
FIG. 8 is cross section of a reference capacitor of FIG. 5 taken along lines 8-8 according to one embodiment.

FIG. 8 is a cross-section of the reference capacitor 32 taken along lines 8-8 of FIG. 5. The reference capacitor 32 is substantially identical to the sensor capacitor 20 of FIG. 7. The bottom electrode 22b of the reference capacitor 32 contacts metal track 54c at contact area 50d. The metal track 54c is in electrical contact with metal via 56c. The top electrode 24b of the reference capacitor 32 contacts metal track 54d and the metal track 56d at contact region 52b. The capacitance of the reference capacitor 32 can be measured through vias 56c, 56e which are electrically connected to the top electrode 24b and the bottom electrode 22b of the reference capacitor 32. The primary difference between the reference capacitor 32 and the sensor capacitor 20 is that the dielectric layers 46, 42 have not been etched to form openings 29 therein. Openings 29 are only formed in the top electrode 24b of the reference capacitor 32. The humidity sensitive dielectric layer 26 is not exposed to the surrounding environment and, therefore, the capacitance of the reference capacitor 32 will not change with a change in humidity.

Figure 9:
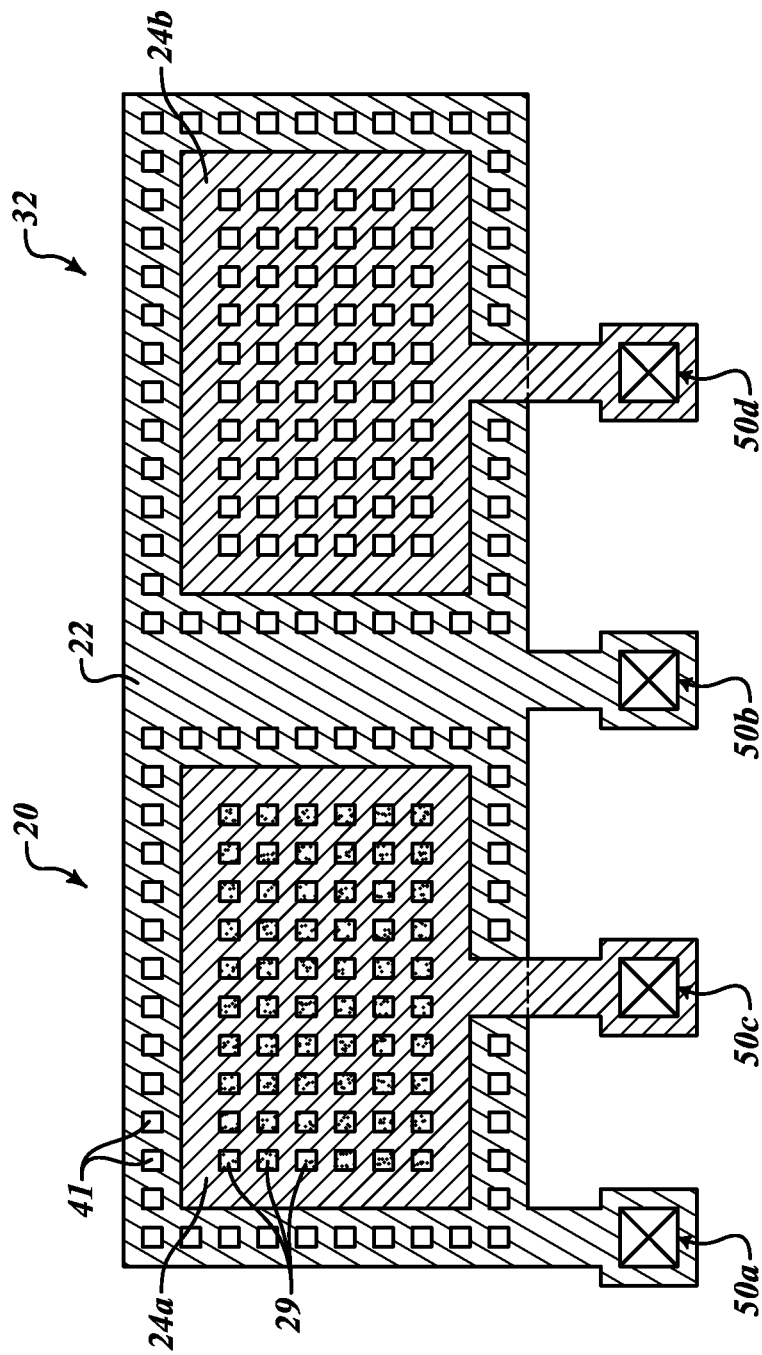
FIG. 9 is a top view of a capacitive humidity sensor and a reference capacitor according to one embodiment.

FIG. 9 is a top view of a sensor capacitor 20 which is a capacitive humidity sensor and a reference capacitor 32. Only the metal layers used to form the bottom electrode 22 and the top electrodes 24a, 24b of the capacitors 20, 32 are shown. In FIG. 9, a single bottom electrode 22 serves as the bottom electrode for the reference capacitor 32 and the sensor capacitor 20. Top electrode 24a is formed over a portion of the bottom electrode 22. Top electrode 24b of the reference capacitor 32 is formed over a separate portion of the bottom electrode 22. Openings 41 in the bottom electrode 22 are formed as described previously to enable adhesion of the humidity sensitive dielectric layer 26 (not shown) to the dielectric substrate 40 below the bottom electrode 22. Openings 29 have been formed in the top electrode 24a of the sensor capacitor 20 and in the top electrode 24b of the reference capacitor 32. Openings 29 in the sensor capacitor 20 expose the humidity sensitive dielectric layer 26 to the surrounding environment. The humidity sensitive dielectric layer 26 has only been shown in the openings 29 in the top electrode 24a of the sensor capacitor 20. In practice, the humidity sensitive dielectric layer 26 would cover the entirety of the bottom electrode 22. The humidity sensitive dielectric layer 26 is not illustrated in the holes 29 of the top electrode 24b of the reference capacitor 32 because the openings 29 in the top plate of the top electrode 24b do not expose the humidity sensitive dielectric layer 26. Though not illustrated in FIG. 9, holes 41 are also formed directly below the holes 29 of both the top electrode 24a and the top electrode 24b.

In one embodiment, the openings 29 in the top electrodes 24a, 24b are about 9 µm wide. The holes 29 in the top electrode 24a and the top electrode 24b are spaced apart by about 16 µm edge to edge. The openings 41 in the bottom electrode 22 are the same size as the opening 29 in the top electrodes 24a, 24b. Alternatively, the openings 41 in the bottom electrode 22 may be slightly larger than the openings 29 in the top electrodes 24a, 24b. In one example, the openings 41 in the bottom electrode 22 are about 15 μm wide in order to allow for some mismatch in the alignments of the masks used to form the openings 29, 41. The openings 29, 41 are shown having square cross-sections. However, the cross-sections may be circular, elliptical, or any other suitable cross-section. A current may be passed through the bottom electrode 22 through contacts 50a, 50b. The top electrode 24a of the sensor capacitor 20 can be electrically contacted at contact region 50c. The top electrode 24b of the reference capacitor 32 can be electrically contacted through contact 50d. Variations between the reference capacitor 32 and the sensor capacitor 20 can be reduced by forming the bottom electrode 22 of the sensor and reference capacitors 20, 32 from single metal plate. When the microcontroller 38 computes a value of the humidity based on the digital humidity signal and the digital control signal, as described previously, it is very beneficial to have a digital control signal that has as little variation as possible from the digital humidity signal except in a component of the digital humidity signal contributed by the change in dielectric constant of the humidity sensitive dielectric layer 26.

Figure 10:
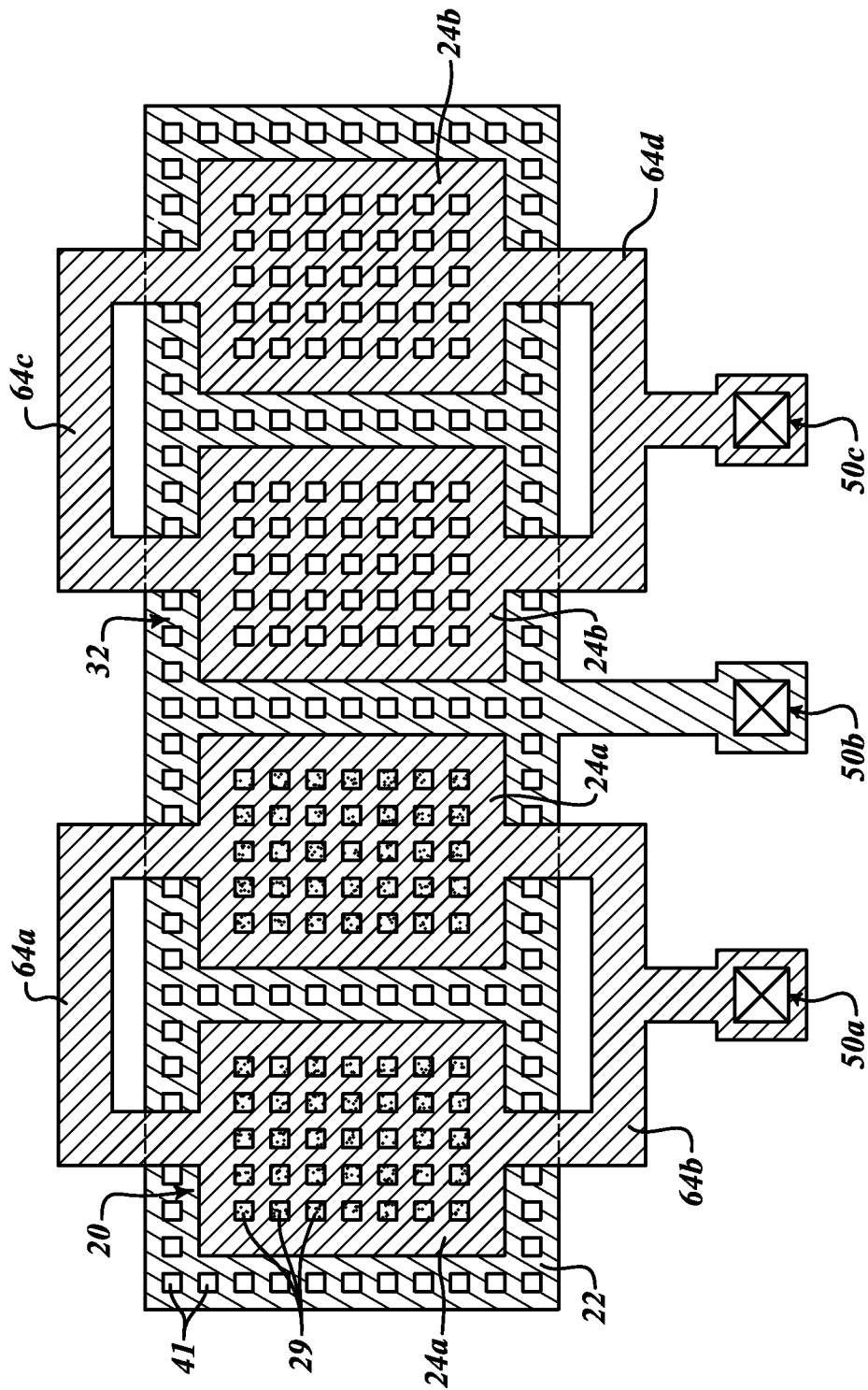
FIG. 10 is a top view of a capacitive humidity sensor including two sensor capacitors and two reference capacitors according to one embodiment.

FIG. 10 is a top view of a sensor capacitor 20 and a reference capacitor 32, according to one embodiment. In FIG. 10, the sensor capacitor 20 and the reference capacitor 32 have a common bottom electrode 22. The sensor capacitor 20 has two adjacent top plates 24a connected by conductive tracks 64a, 64b. The reference capacitor 32 includes two adjacent top plates 24b. The two adjacent top plate portions 24b of the reference capacitor 32 are connected to each other by conductive tracks 64c, 64d. Having two top plate portions 24a, 24b for the sensor capacitor 20 and the reference capacitor 32 helps to compensate for capacitance variations in individual sensor and reference capacitor 20, 32. The common bottom plate 22 can be electrically contacted by contact 50b. The top plates 24a of the sensor capacitor 20 can be contacted through contact 50a. The top plates 24b of reference capacitor 32 can be contacted through contact 50c. In FIG. 10, the conductive tracks 64a-64a are shown as being formed in the same metal layer as the top electrodes 24a, 24b. However, in one embodiment, the metal tracks 64a-64d are formed of a higher metal layer than the top electrodes 24a, 24b and contact the top electrodes 24a, 24b at selected contact regions.

Figure 11:
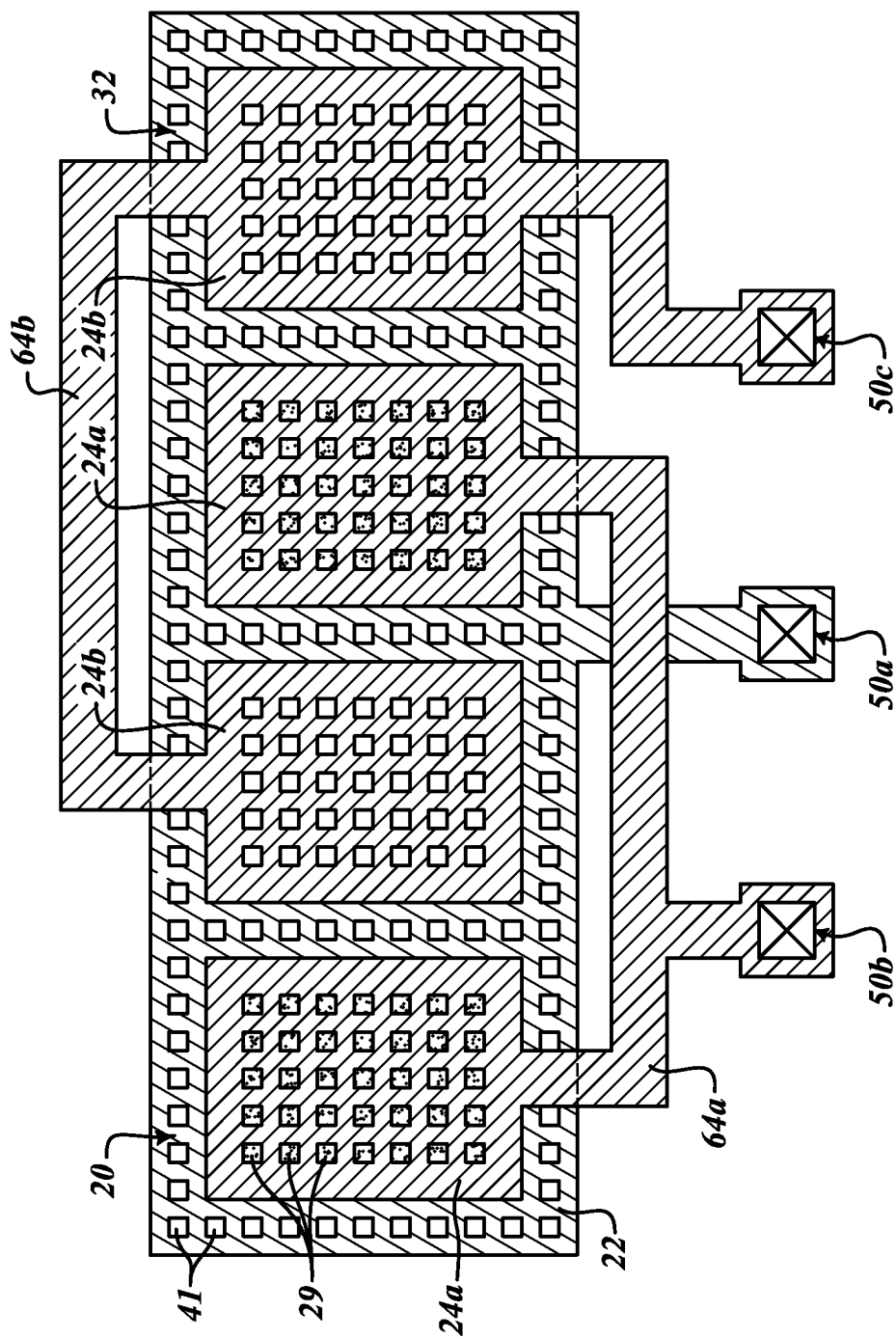
FIG. 11 is a top view of a capacitive humidity sensor including two sensor capacitors and two reference capacitors according to an alternate embodiment.

FIG. 11 illustrates a sensor capacitor 20 and a reference capacitor 32 according to one embodiment. The sensor capacitor 20 includes two top plates 24a. The reference capacitor 32 includes two top plates 24b. The two top plates 24a of the sensor capacitor 20 are separated by one of the top plates 24b of the reference capacitor 32. The two top plates 24a of the sensor capacitor 20 are connected to each other by a conductive track 64a. The two top plates 24b of the reference capacitor 32 are separated from each other by one of the top plates 24a of the sensor capacitor 20. The two top plates 24b of the reference capacitor 32 are connected to each other by conductive tracks 64b. The configuration of the reference capacitor 32 and the sensor capacitor 20 in FIG. 11 further helps to compensate for capacitance variations in individual sensor and reference capacitors. This helps to enable computation of a more accurate value of the humidity in the surrounding environment. Contacts 50a-50c allow for electrical connection to the common bottom plate 22 and to plates 24a, 24b of the reference capacitor 32 and the sensor capacitor 20.

Figure 12:
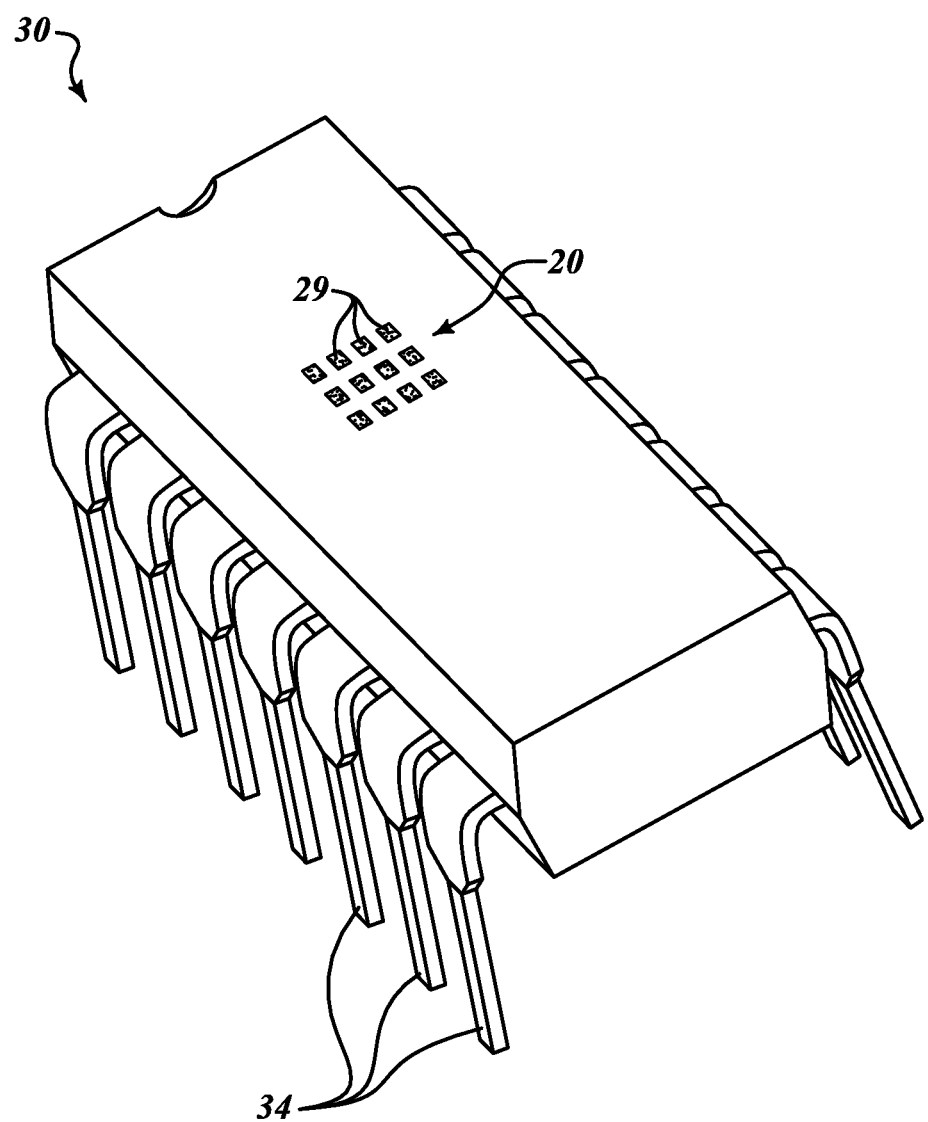
FIG. 12 is an elevated perspective view of a capacitive humidity sensor package according to one embodiment.

FIG. 12 illustrates an integrated circuit package 30 according to one embodiment. The integrated circuit package 30 includes a capacitive humidity sensor 20 as described previously. The capacitive humidity sensor 20 is formed on an integrated circuit die which is encapsulated in the integrated circuit package 30. The humidity sensitive dielectric layer 26 is exposed to the environment surrounding the integrated circuit package 30 by openings 29 formed in the passivation layer 46 encapsulating the integrated circuit package 30. Electrical contacts 34, shown as leads of lead frame in FIG. 12, allow for electrical connection to the capacitive humidity sensor 20. Electrical contacts 24 also allow electrical connection to a microcontroller 38 formed in an integrated circuit die within the integrated circuit package 30. A reference capacitor 32 is also formed in the integrated circuit package 30 but is not exposed to the surrounding environment as described previously. The integrated circuit package 30 shown as a lead frame package in FIG. 12, alternatively may be a ball grid array package, a pin grid array package, an embedded wafer level ball grid array package or any other suitable integrated circuit package.

Figure 13:
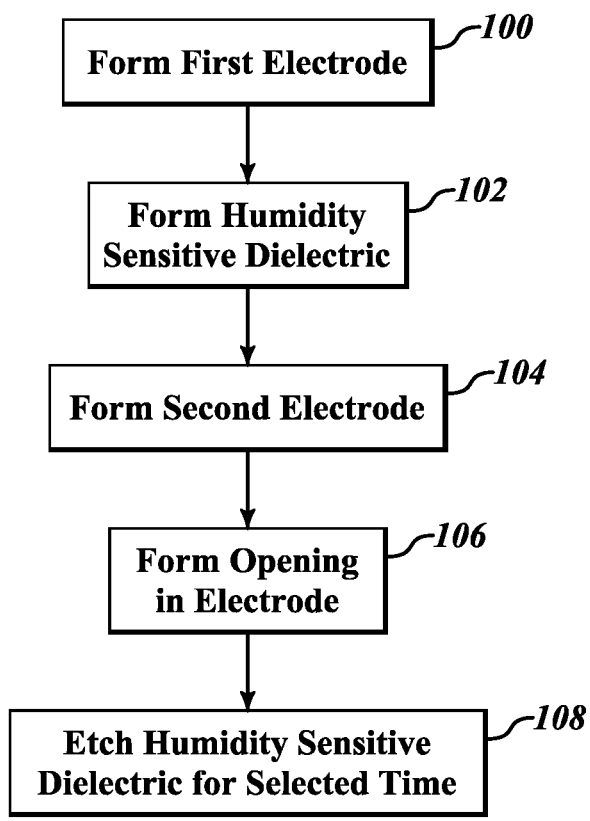
FIG. 13 illustrates a process for forming a capacitive humidity sensor according to one embodiment.

FIG. 13 illustrates a method for forming a capacitive humidity sensor 20 according to one embodiment. At 100, a first electrode 22 is formed on a dielectric substrate 40. The first electrode is patterned to expose portions of the dielectric substrate 40. The first electrode is, for example, tantalum aluminum. The first electrode 22 may also be a heating element as described previously. At 102, a humidity sensitive dielectric layer 26 is formed on the first electrode. The humidity sensitive dielectric layer 26 contacts the dielectric substrate through the openings 41 formed in the first electrode 22. The humidity sensitive dielectric layer 26 has a dielectric content which changes as the humidity sensitive dielectric layer 26 absorbs moisture. The humidity sensitive dielectric layer 26 is, for example, polyimide as described previously. At 104, a second electrode 24 is formed on the humidity sensitive dielectric layer 26. The second electrode 24 is, for example, aluminum. At 106, an opening is formed in the second electrode 24. The opening exposes a portion of the humidity sensitive dielectric layer 26. At 108, the humidity sensitive dielectric layer 26 is isotropically etched through the opening 29 in the second electrode 24. The isotropic etch of the humidity sensitive dielectric layer 26 causes hollow portions to be formed between the first electrode 22 and the second electrode 24. The capacitance of the capacitive humidity sensor 20 can be selected by selecting the duration of the isotropic etch of the humidity sensitive dielectric layer 26. By selecting a longer duration of the isotropic etch, the capacitance of the capacitive humidity sensor 20 can be made comparatively small. By selecting a smaller duration of the isotropic of the humidity sensitive dielectric layer 26, the capacitance of the capacitive humidity sensor 20 can be made comparatively large.

Figure 14:
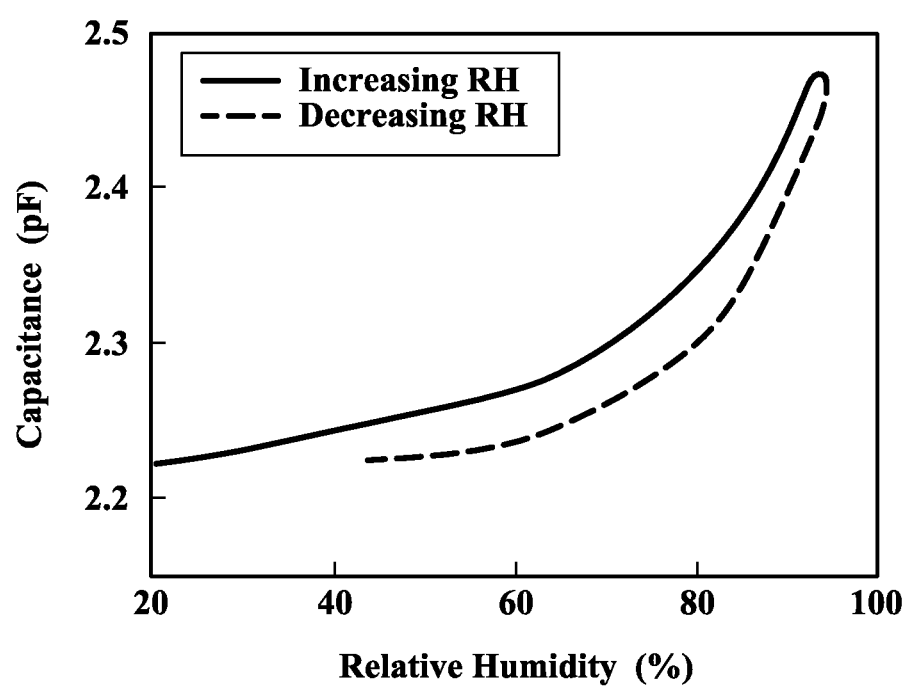
FIG. 14 is a graph of capacitance vs. relative humidity according to one embodiment.

FIG. 14 is a graph of the capacitance of a capacitive humidity sensor 20 vs. relative humidity (RH). The solid black line illustrates the relative humidity of the capacitive humidity sensor 20 while the relative humidity is increasing. The capacitance follows a nearly linear curve from 0% RH to about 70% RH. Between about 70% and 100% RH the capacitance follows a somewhat exponential curve. The capacitance of the capacitive humidity sensor 20 varies from about 2.2 pF at 0% humidity to about 2.5 pF at 100% humidity.

The graph of FIG. 14 illustrates that the capacitive humidity sensor 20 exhibits hysteretic effects. The capacitance of the capacitive humidity sensor 20 follows a different curve, shown in dashed lines, when decreasing from 100% RH. For this reason it is beneficial to utilize a heating element to expel humidity from the humidity sensitive dielectric layer 26 prior to making a new measurement of the humidity. Prior to taking a new measurement of humidity, a current is passed through the bottom electrode 22 of the capacitive humidity sensor 20 to expel moisture from the humidity sensitive dielectric layer 26. After passing the current through the bottom electrode 22, a brief time can be allowed for the humidity sensitive dielectric layer 26 to absorb moisture from the air before taking the new humidity measurement.

As can be seen in the graph of FIG. 14, the sensitivity of the sensor for polyimide can be easily measured over a range from 20% to 100%, with the greatest sensitivity being over 60% when large recesses 28 are formed. While not shown on the graph, reliable measurements can also be made with polyimide over the range of a humidity from 0% to 20% and the controlled size of hollow portions 28 increases the sensitivity selection in this range more than is possible with only polyimide as the dielectric. Of course, other humidity sensitive dielectrics can be used in place of polyimide that provide improved sensitivity over the range of 0% to 50% humidity. Such materials include undoped silicon, nanoporous silicon, ceramics, porous ceramics, glass, aerogels, nanoporous silicon dioxide compositions, and the like.

According to one embodiment, two humidity sensitive capacitors having different ranges for peak sensitivity are placed adjacent to each other on the same integrated circuit. One capacitor has a dielectric with a very sensitive response in the 0% to 60% range and adjacent to it is another capacitor having a very sensitive response in the 50% to 100% range. The circuit 38 can use data from just one of the sensors to determine the humidity, selecting the one with the most sensitivity for the measured humidity, or alternatively, it can use data from both to aid in arriving at the most reliable and accurate humidity measurement.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device comprising:
a first electrode acting as a heating element, wherein the first electrode is a tantalum aluminum resistor;
a second electrode above the first electrode; and
a humidity sensitive dielectric material whose dielectric constant varies based on the ambient humidity, the humidity sensitive dielectric material being positioned between the first electrode and the second electrode;
at least one aperture extending through the second electrode; and
a recess in the humidity sensitive dielectric material that forms a hollow region between the first electrode and the second electrode, extending under a portion of second electrode, the humidity sensitive dielectric having a first thickness at the recess and a second, greater thickness in the locations spaced from the recess, wherein the first electrode is configured to heat the humidity sensitive dielectric material.

2. The device of claim 1 comprising an opening in the first electrode, positioned directly below a corresponding aperture in the second electrode.

3. The device of claim 1 wherein the humidity sensitive dielectric material is polyimide.

4. The device of claim 1 comprising a plurality of apertures in the second electrode configured to expose the humidity sensitive dielectric material over a large area to an ambient gas environment surrounding the device.

5. The device of claim 1 wherein the first and second electrodes output an analog signal indicative of humidity of an environment in which the device is placed.

6. The device of claim 5 wherein the first electrode, the humidity sensitive dielectric material, and the second electrode comprise a capacitive humidity sensor.

7. The device of claim 6 comprising a reference capacitor adjacent the capacitive humidity sensor, the reference capacitor being configured to output a reference capacitance signal.

8. A device comprising:
a dielectric substrate;
a first electrode above the dielectric substrate;
a second electrode above the first electrode; and
a humidity sensitive dielectric material whose dielectric constant varies based on the ambient humidity positioned on the first electrode and positioned between the first electrode and the second electrode, the humidity sensitive dielectric material contacting the dielectric substrate;
at least one aperture extending through the second electrode;
a recess in the humidity sensitive dielectric material that forms a hollow region between the first electrode and the second electrode, extending under a portion of the second electrode, the humidity sensitive dielectric having a first thickness at the recess and a second greater thickness in the locations spaced from the recess; and
a passivation layer over the second electrode, the passivation layer being patterned to expose the opening in the second electrode.

9. A method comprising:
forming a first electrode on a dielectric substrate;
depositing a humidity sensitive dielectric material on the first electrode;
forming a second electrode on the humidity sensitive dielectric material above the first electrode;
removing a portion of the humidity sensitive dielectric material to form a hollow region between the first and second electrodes;
forming a passivation layer over the second electrode;
etching the passivation layer and the second electrode to expose a portion of the humidity sensitive dielectric material;
forming a third electrode on the dielectric substrate;
forming a fourth electrode on the humidity sensitive dielectric material; and
masking a portion of the passivation layer to prevent etching of the passivation layer over the fourth electrode.

10. The method of claim 9 wherein the first and second electrodes are configured to emit a capacitive signal indicative of humidity.

11. The method of claim 9 wherein removing the portion of the humidity sensitive dielectric layer comprises isotropically etching the humidity sensitive dielectric material.

12. The method of claim 11 comprising selecting a duration of the step of isotropically etching to achieve a desired value of a capacitance between the first and the second electrode.

13. The method of claim 11 wherein isotropically etching the humidity sensitive dielectric layer comprises isotropically etching the humidity sensitive dielectric material in a plurality of separate locations.

14. A method comprising:
forming a first electrode on a dielectric substrate;
removing a portion of the first electrode to expose a portion of the dielectric substrate;
depositing a humidity sensitive dielectric material on the first electrode and the exposed portion of the dielectric substrate;
forming a second electrode on the humidity sensitive dielectric material above the first electrode;
removing a portion of the humidity sensitive dielectric material to form a hollow region between the first and second electrodes; and
forming first and second contact regions on the bottom electrode, the first and second electrodes being configured to pass a current from the first contact region through the bottom electrode to the second contact region to heat humidity sensitive dielectric material comprises passing a current through the first electrode.

15. A method comprising:
forming a first electrode on a dielectric substrate;
removing a portion of the first electrode to expose a portion of the dielectric substrate;
depositing a humidity sensitive dielectric material on the first electrode and the exposed portion of the dielectric substrate, the humidity sensitive dielectric material contacting the exposed portion of the dielectric layer;
forming a second electrode on the humidity sensitive dielectric material above the first electrode; and
removing a portion of the humidity sensitive dielectric material to form a hollow region between the first and second electrodes, wherein the humidity sensitive dielectric layer is polyimide.

16. A capacitive humidity sensor comprising:
a dielectric substrate;
a first capacitor electrode on the dielectric substrate;
a humidity sensitive dielectric material on the first capacitor electrode;
a second capacitor electrode on the humidity sensitive dielectric;
a passivation layer on the second electrode, the passivation layer and the second electrode having openings therein to expose the humidity sensitive dielectric material, the humidity sensitive dielectric layer having recesses therein forming hollow regions between the first and second capacitor electrodes; and
a heater adjacent the humidity sensitive dielectric material, the heater configured to heat the humidity sensitive dielectric material to release humidity from the humidity sensitive dielectric layer.

17. The capacitive humidity sensor of claim 16 comprising a reference capacitor, the reference capacitor including:
a third capacitor electrode on the dielectric substrate and below the humidity sensitive dielectric layer; and
a fourth capacitor electrode on the humidity sensitive dielectric layer, the passivation layer being on the fourth capacitor electrode and to preventing exposure of the humidity sensitive layer to air.

18. The capacitive humidity sensor of claim 17 comprising:
an analog to digital converter configured to receive an analog humidity signal from the first and second capacitor electrodes, and to convert the analog humidity signal to a digital humidity signal; and
a microcontroller configured to receive the digital humidity signal from the analog to digital converter and to estimate a value of a humidity in an environment surrounding the capacitive humidity sensor based on the digital humidity signal.

* * * * *